United States Patent [19]

Schinazi et al.

[11] Patent Number: 5,599,796
[45] Date of Patent: Feb. 4, 1997

[54] TREATMENT OF UROGENITAL CANCER WITH BORON NEUTRON CAPTURE THERAPY

[75] Inventors: Raymond F. Schinazi, Decatur; Thomas E. Keane, Dunwoody; Dennis C. Liotta, McDonough, all of Ga.

[73] Assignee: Emory University, Atlanta, Ga.

[21] Appl. No.: 334,759

[22] Filed: Nov. 4, 1994

Related U.S. Application Data

[63] Continuation-in-part of Ser. No. 161,674, Dec. 2, 1993.
[51] Int. Cl.$^6$ .......................... A61K 31/69; A61K 41/00; A61K 43/00
[52] U.S. Cl. .............................. 514/44; 514/47; 514/48; 514/51; 514/52; 514/64; 424/1.11; 424/1.73; 424/1.81; 604/20
[58] Field of Search .................................. 514/45, 46, 47, 514/48, 49, 50, 51, 64, 52; 424/1.11, 9, 1.73, 1.81; 604/20

[56] References Cited

U.S. PATENT DOCUMENTS

| | | | |
|---|---|---|---|
| 4,516,535 | 5/1985 | Russell, Jr. et al. | 128/1.1 |
| 4,855,493 | 8/1989 | Spielvogel et al. | 562/575 |
| 4,959,356 | 9/1990 | Miura et al. | 514/64 |
| 5,021,572 | 6/1991 | Gabel | 544/229 |
| 5,066,479 | 11/1991 | Hawthorne | 424/1.1 |
| 5,130,302 | 7/1992 | Spielvogel et al. | 514/45 |
| 5,272,250 | 12/1993 | Spielvogel et al. | 530/300 |
| 5,328,678 | 7/1994 | Fujii et al. | 424/1.21 |
| 5,405,598 | 4/1995 | Schinazi et al. | 424/1.81 |

FOREIGN PATENT DOCUMENTS

WO93/17028  9/1993  WIPO.

OTHER PUBLICATIONS

Barth, et al., "Boron Neutron Capture Therapy of Cancer," *Cancer Res.*, 50:1061–1070 (1990).

Barth, R. F.; Soloway, A. H.; Fairchild, R. G.; Brugger, R. M., "Boron Neutron Capture Therapy," *Cancer*, 70:2995–3008 (1992).

Cotton and Wilkinson, *Advanced Inorganic Chemistry*, Fourth Editon, John Wiley and Sons, 318–320 (1980).

Fairchild, R. G., et al., "In Vitro Determination of Uptake, Retention, Distribution, Biological Efficacy, and Toxicity of Boronated Compounds for Neutron Capture Therapy: A Comparison of Porphyrins with Sulfhydryl Boron Hydrides," *Cancer Res.*, 50:4860–4865 (1990).

Fairchild, R. G., Gabel, D., Laster, B., and Kiszenick, W. "Boron–10 Analysis by Prompt–gamma and Track Etching Techniques", the First International Symposium on Neutron Capture Therapy, Oct. 12–14, 1983.

Fulcrand–El Kattan, et al., "Carboranyl Oligonucleotides. 2. Synthesis and Physiocochemical Properties of Dodecathymidylate Containing 4–(o–Carboran–1–yl)–2'–deoxyuridine," *J. Am. Chem. Soc.*, 116(17):7494–7501 (1994).

Gabel, D., Hocke, I., and Elsen, W., "Determination of sub–ppm amounts of boron–10 solutions by means of solid state track detectors," *Phys. Med. Biol.*, 28:1453–1457 (1983).

Goudgaon, N. M., El–Kattan, G. F., and Schinazi, R. F., "Boron containing pyrimidines, nucleosides, and oligonucleotides for neutron capture therapy," *Nucleosides & Nucleotides*, 13:849–880 (1994).

Hatanaka and Sano, "A Revised Boron–Neutron Capture Therapy for Malignant Brain Tumours," *Z. Neurol.*, 204:309–332 (1973).

Hawthorne, "The Role of Chemistry in the Development of Boron Neutron Capture Therapy of Cancer," *Angew. Chem. Int. Ed. Engl.* 32:950–984 (1993).

Heying, T. L. et al., "A new series of organoboranes. (I) Carboranes from the reaction of decaborane with acetylenic compounds," *Inorg. Chem.* 1963, 2, 1089–1092.

Keane, T. E., et al., "Combination versus single agent therapy in effecting complete therapeutic response in human bladder cancer: analysis of cisplatin and/or 5–fluorouracil in an in vivo survival model," *Cancer Res.*, 54:475–481 (1994).

(List continued on next page.)

Primary Examiner—James O. Wilson
Attorney, Agent, or Firm—Kilpatrick & Cody; Sherry M. Knowles

[57] ABSTRACT

Methods and compositions for treating urogenital tumors, and particular, cancer of the prostate, bladder, and kidney, with BCNT, are disclosed. Any boron-containing compound that is sufficiently lipophilic to pass through the appropriate urogenital membranes in a quantity high enough to achieve therapy on irradiation with low-energy neutrons can be used. Carboranyl-containing nucleosides and oligonucleotides are particularly suited for use in BNCT of urogenital tumors. Preferred compounds include 5-carboranyl-2'-deoxyuridine (CDU) and 5-o-carboranyl-1-(2-deoxy-2-fluoro-β-D-arabinofuranosyl)uracil (CFAU). Nucleosides and oligonucleotides bearing an -O-[(carboran-1-yl)alkyl]phosphate, S-[(carboran-1-yl)alkyl]phosphorothioate, or Se-[(carboran-1-yl)alkyl]phosphoroselenoate in place of the (carboran-1-yl)phosphonate moiety can be used. Oligonucleotides of specific gene sequences that include one or more 3',5'-linking-(carboran-1-yl)phosphonate moieties can also be used in antisense therapy in the selective modification of gene expression. Compounds can be used in urogenital BNCT therapy that contain boron clusters as a means to enhance lipophilicity wherein the boron is not enriched in $^{10}$B, but instead, in the $^{11}$B isotope. The therapy is accomplished by administering the boron-containing compound by any appropriate route, including by intravenous injection, oral delivery or by catheter or other direct means, in such a manner that the compound accumulates in the target tumor. After desired accumulation of the compound in the tumor, the site is irradiated with an effective amount of low energy neutrons.

21 Claims, 7 Drawing Sheets

OTHER PUBLICATIONS

Keane, T. E., Rosner, G., Gingrich, J., Poulton, S., and Walther, P., "The therapeutic impact of dipyridamole: chemopotentiation of the cytotoxic combination 5–fluorouracil/cisplatin in an animal model of human bladder cancer," *J. Urol.*, 146:1418–1424 (1991).

Keane, T. E., Rosner, G., Donaldson, J., Norwood, D., Poulton, S. H., and Walther, P. J., "Dipyridamole–cisplatin potentiation in xenograft models of human testicular and bladder cancer," *J. Urol.*, 144:1004–1009 (1990).

Lesnikowski, Z. J., "Stereocontrolled Synthesis of P–Chiral Analogues of Oligonucleotides," *Bioorganic Chem., 21:127–155 (1993).*

Marshall and Caruthers, "Phosphorodithioate DNA as a Potential Therapeutic Drug," *Science* 259:1564–1570 (1993).

Milligan, J. F., Matteucci, M. D., Martin, J. C., "Current Concepts in Antisense Drug Design," *J. Med. Chem.*, 36(14):1923–1937 (1993).

Reynolds, R. C.; Trask, T. W.; Sedwick, W. D., "2,4–Dichloro–5–(1–o–carboranlymethyl)–6–methylpyrimidine: A Potential Synthon for 5–(1–o–Carboranylmethyl)pyrimidines," *J. org. Chem.* 56:2391–2395 (1991).

Schinazi, R. F., Prusoff, W. H., "Synthesis and Properties of Boron and Silicon Substituted Uracil or 2'–Deoxyuridine," *Tetrahedron Lett* 50:4981–4984 (1978).

Schinazi, R. F., et al., "Synthesis Antiviral Activity Cytotoxicity, and Cellular Pharmacology of 5–Carboranyl–Pyrimidine Nucleosides," *Advances in Neutron Capture Therapy*, Plenum Press:New York and London, pp. 285–288 (1993).

Schinazi, R. F., et al., "Synthesis, Biological Activity, and Cellular Pharmacology of 5–Carboranyl–Pyrimidine Nucleosides," Tenth International Roundtable: Nucleosides and Nucleotides, Park City, Utah; p. 28 (1992).

Schinazi, R. F.; Prusoff, W. H., "Synthesis of 5–(Dihydroxyboryl)–2'–deoxyuridine and Related Boron–Containing Pyrimidines," *J. Org. Chem.*, 50:841–847 (1985).

Sood, A., Spielvogel, B. F.; Shaw, B. R. J., "Boron–Containing Nucleic Acids; Synthesis of Cyanoborane Adducts of 2'–Deoxynucleosides," *Am. Chem. Soc.* 111:9234–9235 (1989).

Sood, A.; Shaw, B. R.; Spielvogel, B. F., "Boron–Containing Nucleic Acids. 2. 1 Synthesis of Oligodeoxynucleoside Boranophosphates," *J. Am. Chem. Soc.* 112:9000–9001 (1990).

Su, et al., "Nucleosides. 136. Synthesis and Antiviral Effects of Several 1–(2–Deoxy–20fluoro–B–D–arabinofuranosyl)–5–alkyluracils. Some Structure–Activity Relationships," *J. Med. Chem.*, 29:151–154 (1986).

Tolpin, et al., "Boron Neutron Capture Therapy of Cerebral Gliomas," *Oncology*, 32:223–246 (1975).

Uhlmann and Peyman, "Antisense Oligonucleotides: A New Therapeutic Principle" *Chemical Reviews*, 90(4):544–584 (Jun. 1990).

Vorbruggen, H. and Hofle, G., "On the mechanism of nucleoside synthesis," *Chem. Ber.* 114:1256–1268 (1981).

Van Roev, P., et al., "Absolute configuration of the antiviral agent (–)–cis–5–fluoro–1–[2–hydroxymethyl)–1,3–oxathiolan–5–yl]cytosine," *Antiviral Chem. Chemotherapy*, 4:369–375 (1993).

Wilson and Liotta, "A general method for controlling glycosylation sterochemistry in the synthesis of 2'–deoxyribose nucleosides," *Tetrahedron Lett.*, 31:1815–1818 (1990).

Wilson, J. G., "Synthetic Approaches to a Carboranyl Thiouracil," *Pigment Cell Res.*, 2:297–303 (1989).

Yamamoto, et al., "Synthesis of Carboranes Containing Nucleoside Bases. Unexpectedly High Cytostatic and Cytocidal Toxicity towards Cancer Cells," *J. Chem. Soc., Chem. Commun.*, 157–158 (1992).

Yamamoto, Y.; Seko, T.; Nakamura, H., "Synthesis of Varboranes Containing Nucleoside Bases." *Heteroatom, Chem.*, 3:239–244 (1992).

Zamenhof, R. G.; Kalend, A. M.; and Bloomer, W. D., "BNCT: Looking for a Few Good Molecules," *J. Nat'l. Cancer Inst.*, 84:1290–1291 (1992).

"N.Y. cancer patient fights for novel radiation therapy," *The Atlanta Journal/The Atlanta Constitution*, Sep. 17, 1994.

α (a) BzCl/pyridine; (b) HC≡CSi(Me)$_3$, PdCl$_2$(PPh$_3$)$_2$, Et$_3$N/THF; (c) TBAF/THF; (d) B$_{10}$H$_{12}$(CH$_3$CH$_2$CN)$_2$ / toluene; (e) MeONa/MeOH.

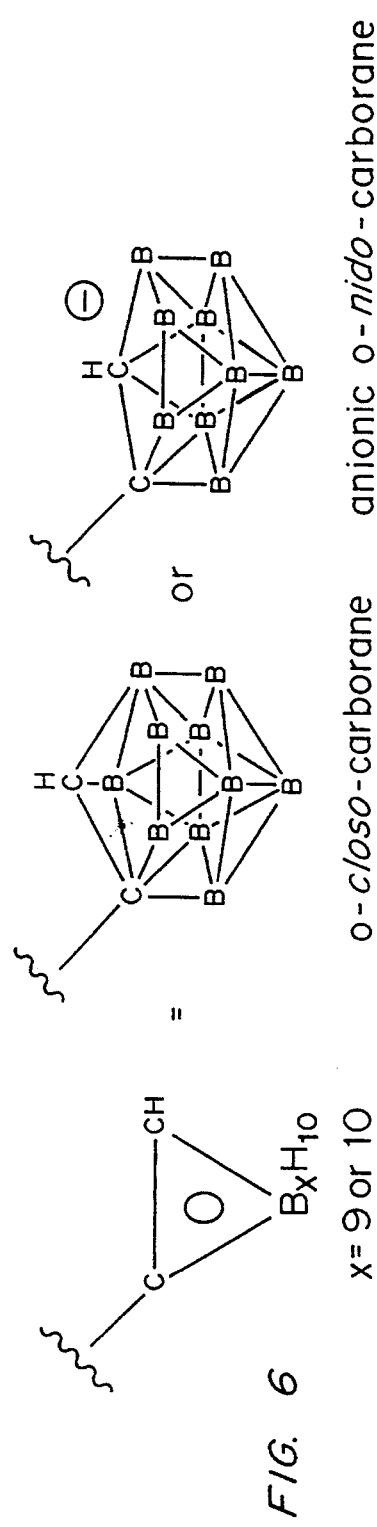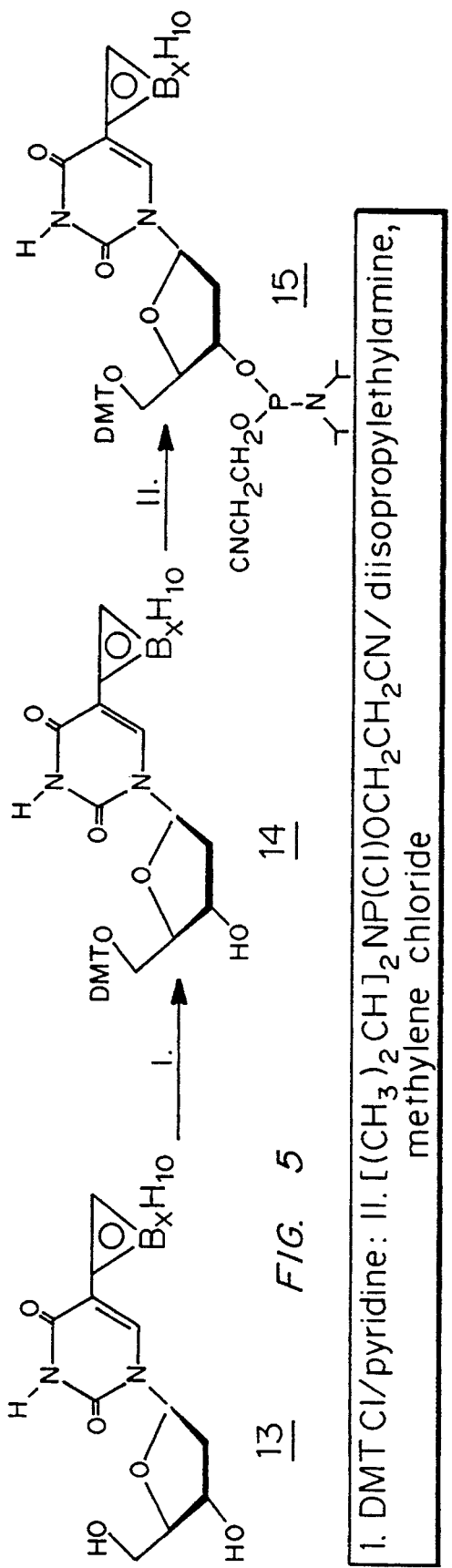
FIG. 6
FIG. 5

TREATMENT OF UROGENITAL CANCER WITH BORON NEUTRON CAPTURE THERAPY

The United States Government has rights to this invention pursuant to Grant Number CA53892 by the National Institutes of Health.

This invention is in area of treatment of urogenital cancer with boron neutron capture therapy.

BACKGROUND OF THE INVENTION

This application is a continuation-in-part of U.S. Ser. No. 08/161,674, filed on Dec. 2, 1993, by Raymond F. Schinazi, Geraldine Fulcrand-El Kattan and Zbigeniew Jan Lesnikowski, directed to Nucleosides and Oligonucleotides Containing Boron Clusters.

A. BNCT and its Prior Uses

The goal of cancer therapy is to achieve a degree of selectivity that spares normal cells and destroys all malignant ones, since even a small number of remaining malignant cells can lead to recurrence, metastasis, and death. A two-component or binary system comprised of constituents that alone are nonlethal and largely confined to malignant cells, and which when combined are lethal to the neoplastic cells yet innocuous to normal cells is an ideal modality. One advantage of this type of binary system is that each component can be manipulated independently to maximize selectivity.

Boron neutron capture therapy (BNCT, see FIG. 1) is a binary system which combines two separately nonlethal constituents, a radiosensitizing compound that contains a stable boron-10($^{10}$B) isotope, and nonionizing neutron radiation. When boron-10 is irradiated with neutrons, a nuclear reaction occurs that yields helium nuclei ($\alpha$-particle), lithium nuclei, and about 100 million times more energy than the initial irradiated energy. The generated radiation destroys malignant cells containing the boron compound. Selectivity is achieved through the use of compounds which accumulate primarily in malignant cells and/or by aiming the neutron beam at the tumor mass which contains the boron carrier.

BNCT has historically been used or attempted primarily for brain cancers, and specifically, for glioblastoma multiform, an aggressive malignant brain tumor.

It would be of great benefit to be able to extend the use of BNCT to urogenital tumors, including cancer of the prostate, kidney, and bladder.

Prostate cancer is the most frequently diagnosed carcinoma in the U.S. male population. In 1994 the expected incidence is 200,000 new cases with 40,000 fatalities. Cure is limited to those with early localized disease. Therapeutic modalities include radical surgery, radiotherapy, androgen deprivation, cryotherapy, and observation. Patients presenting with organ confined cancer are candidates for curative surgery or radiotherapy. However, only approximately one third of patients present with truly curable prostate cancer, while the rest have advanced disease which is incurable. Early detection and screening may increase the proportion of patients with curable disease. However, new more effective therapies are necessary for patients with advanced disease.

Deaths attributable to kidney, or renal, cancer has risen in the United States from approximately 5,000 in 1960 to over 10,000 1990. It is estimated that there has been a 35% increase in renal cancer in men and a 16% increase in renal cancer in women in that timeframe. There were approximately 10,000 deaths attributable to bladder cancer in 1994, and an estimated 51,200 new bladder cancer cases reported in that year. The rate of bladder cancer is four times greater among men than women. When detected at an early stage, the 5-year survival rate for bladder cancer is 91%. However, for regional and distant disease, the survival rates are 46% and 9%, respectively. Surgery, alone or in combination with other treatments is currently used in over 90% of bladder cancer. Preoperative chemotherapy alone or with radiation before cystecomy has improved some treatment results.

B. Boron-containing Compounds Reported for Use in BNCT

Many classes of compounds have been synthesized for BNCT. For example, see Barth, R. F.; Soloway, A. H.; Fairchild, R. G.; Brugger, R. M., *Cancer*, 70:2995–3008 (1992); Fairchild, R. G.; Kahl, S. B.; Laster, B. H.; Kalef-Ezra, J.; Popenoe, E. A., *Cancer Res.*, 50:4860–4865 (1990); and Zamenhof, R. G.; Kalend, A. M.; and Bloomer, W. D., *J. Nat'l. Cancer Inst.*, 84:1290–1291 (1992).

Examples of boron-containing compounds include $Na_2B_{12}H_{11}SH$ (sodium borocaptate or BSH), p-carboxybenzeneboronic acid, sodium decahydrodecaborate, $B_{12}H_{11}SH^{2-}$, $B_{10}Cl_9(SH)_2^{2-}$, p-boronophenylalanine, boronated amino and polyamino acids, including boronated polylysine; [N-succinimidyl-3-(undecahydrododeca-boranyldithio)propionate, and carborane-containing amino acids, carborane-containing promazine, carborane-containing porphyrins, and other polyhedral boranes. See Barth, et al., *Cancer*, 70:2995–3008 (1992), and Hawthorne, *Angew. Chem. Int. Ed. Engl.* 1993, 32, 950–984.

The first boron-containing nucleoside, 5-dihydroxyboryl-2'-deoxyuridine, was synthesized by Schinazi and Prusoff in 1978. Schinazi, R. F., Prusoff, W. H., *Tetrahedron Lett.*, 4981–4984 (1978); and Schinazi, R. F.; Prusoff, W. H., *J. Org. Chem.*, 50:841–847 (1985).

Sood, et al. have reported the synthesis of a series of cyanoborane adducts of 2'-deoxynucleosides, specifically 2'deoxyguanosine-$N^7$cyanoborane, 2'-deoxyinosine-$N^7$cyanoborane, 2'-deoxyadenosine-$N^1$-cyanoborane, and 2'-deoxycytidine-$N^3$cyanoborane. Sood, A.; Spielvogel, B. F.; Shaw, B. R., *J. Am. Chem. Soc.*, 111:9234–9235 (1989).

Sood, et al. have also reported the synthesis of oligonucleotides with a boronated internucleotide backbone, in the form of boranophosphates and boranophosphate methyl esters. The borane ($BH_3$) group in these boronated oligonucleotides is isoelectronic and isostructural with normal O-oligonucleotides and oligonucleotide methylphosphonates. Sood, A.; Shaw, B. R.; Spielvogel, B. F., *J. Am. Chem. SOC.*, 112:9000–9001 (1990). The Sood compounds in general have a low boron content and some have lower than desired lipophilicity.

U.S. Pat. No. 5,130,302 to Spielvogel, et al., discloses a novel class of boronated nucleosides, nucleotides and oligonucleotides for use as antineoplastic, antiinflammatory, and antihypertensive agents. The nucleosides, nucleotides and oligonucleotides are covalently attached to either $BH_2CN$, $BH_3$, or $BH_2CO_2R$ moieties, wherein R is $C_1$ to $C_{18}$ alkyl.

A number of carboranyl pyrimidines have been prepared for use in boron neutron capture therapy. Examples of carboranyl pyrimidines include 5-(3-O-carboranylpropyl-6-methyl-2-thiouracil (compound A) (Wilson, J. G., *Pigment Cell Res.*, 2:297–303 (1989)), 2,4-dichloro-5-(1-o-carboranylmethyl)-6-methylpyrimidine; (compound B) (Reynolds, R. C.; Trask, T. W.; Sedwick, W. D. J. Org. Chem., 56:2391–2395 (1991)); and 5-carboranyluracil (compound C) (Goudgaon, N. M.; El-Kattan, Y.; Fulcrand, G.; Liotta, D.C.; Schinazi, R. F., *IMEBORON VIII*, Knoxville, Tenn.; p72 (1993)).

Purine and pyrimidine nucleosides that contain a carboranyl group attached to the purine or pyrimidine base have also been reported. Yamamoto, Y.; Seko, T.; Nakamura, H., *Heteroatom Chem.*, 3:239–244 (1992); and Schinazi, R. F.; Goudgaon, N. M.; Soria, J.; Liotta, D.C., *5th International Symposium on Neutron Capture Therapy*, Columbus, Ohio; p11 (1992); Schinazi, R. F.; Goudgaon, N.; Soria, J.; Liotta, D.C., *Tenth International Roundtable: Nucleosides and Nucleotides*, Park City, Utah; p28 (1992). These compounds are lipophilic and some are readily phosphorylated by cellular kinases, and in certain cells can incorporate into DNA as analogues of natural 2'-deoxypyrimidine nucleosides. Examples include 5-carboranyl-2'-deoxyuridine (compound D, CDU), 5-carboranyluridine (compound E, CU), 5-(1-hydroxymethyl)carboranyluridine, and 5-(1-hydroxymethyl)carboranyluridine (compound F, HMCU).

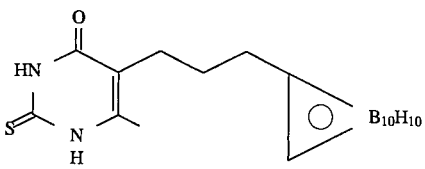

A

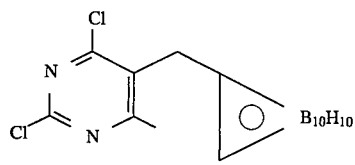

B

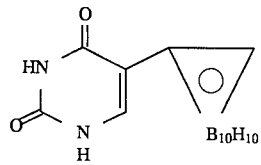

C

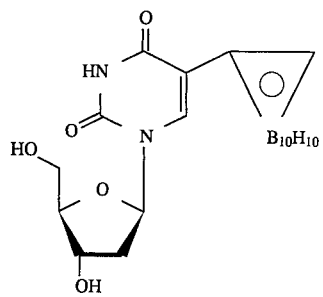

D

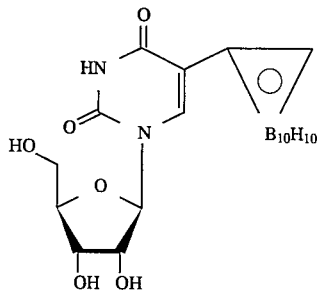

E

-continued

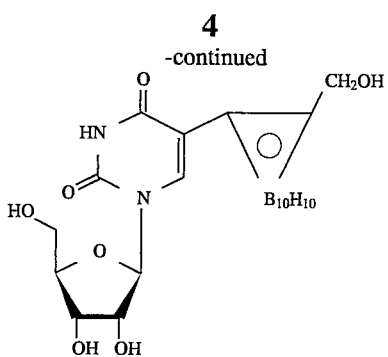

F

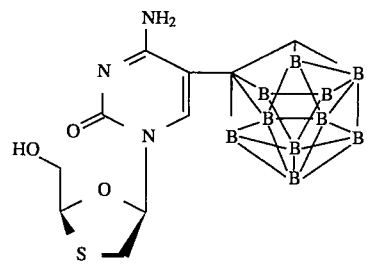

G

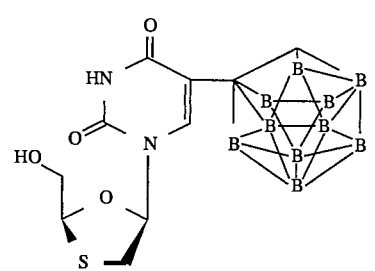

H

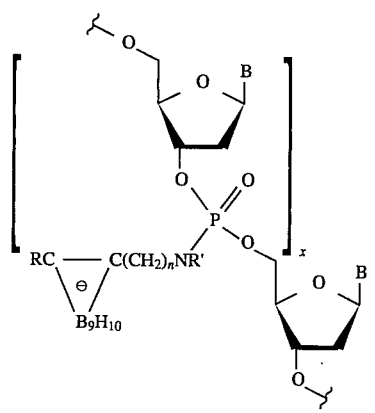

I

PCT WO 93/17028 filed by Raymond F. Schinazi and Dennis C. Liotta discloses a number of synthetic nucleosides that contain a carboranyl moiety covalently attached to a purine or pyrimidine base, wherein the sugar moiety optionally contains a second heteroatom in the 3'-position of the ring. Preferred compounds are 2-hydroxymethyl-5-(5-carboranylcytosin-1-yl)-1,3-oxathiolane (compound G) and 2-hydroxymethyl-5-(5-carboranyluridin-1-yl)-1,3-oxathiolane (compound H).

Powell, et al., recently reported the synthesis of oligonucleotides that contain 3',5'-nido-o-carboranyl-phosphoramidate linkages (compound I). While the oligonucleotide could reportedly localize in the cell nucleus, the boron moiety is acid labile because it is linked to the phosphorus atom through an amide-type bond.

C. Antisense Oligonucleotide Therapy

The requirements for efficient BNCT with oligonucleotides, which include cell selectivity (ability to accumulate preferentially in diseased cells), stability of the chemotherapeutic agent in vivo (resistance against digestion by cellular nucleases and chemical stability), and transportability (ability of the chemotherapeutic agent to pass easily through cellular membranes), are very similar to the requirements for Antisense Oligonucleotide Technology (AOT), another recently developed therapy for cancer as well as other diseases. Uhlmann, "Antisense Oligonucleotides: A New Therapeutic Approach" *Chemical Reviews*, 90(4) (June 1990). Antisense technology refers in general to the modulation of gene expression through a process wherein a synthetic oligonucleotide is hybridized to a complementary nucleic acid sequence to inhibit transcription or replication (if the target sequence is DNA), inhibit translation (if the target sequence is RNA) or to inhibit processing (if the target sequence is pre-RNA). A wide variety of cellular activities can be modulated using this technique. A simple example is the inhibition of protein biosynthesis by an antisense oligonucleotide bound to mRNA. In another embodiment, a synthetic oligonucleotide is hybridized to a specific gene sequence in double stranded DNA, forming a triple stranded complex (triplex) that inhibits the expression of that gene sequence. Antisense oligonucleotides can be also used to activate gene expression indirectly by suppressing the biosynthesis of a natural repressor or directly by reducing termination of transcription. AOT can be used to inhibit the expression of pathogenic genes, for example, those that facilitate the replication of viruses, including human immunodeficiency virus (HIV), hepatitis B virus (HBV), and herpes viruses, and cancers, particularly solid tumor masses such as urogenital cancers, gliomas, breast cancer, and melanomas.

An attractive approach to the treatment of urogenital tumors may be to combine aspects of AOT and BCNT using oligonucleotides that will selectively localize in target urogenital cancer cells.

It is therefore an object of the present invention to provide a method for the treatment of urogenital tumors, and in particular, cancer of the prostate, bladder, and kidney, using BNCT.

It is another object of the present invention to provide a method for the treatment of urogenital cancer that includes the combined approaches of AOT and BNCT.

SUMMARY OF THE INVENTION

It has been discovered that boron neutron capture therapy, optionally combined with antisense oligonucleotide therapy, can be used in the treatment of urogenital tumors, and in particular, cancer of the prostate, bladder, and kidney.

The prostate gland is impermeable to many compounds unless they are lipophilic and delivered unbound to serum proteins. It has been found that lipophilic boron-containing compounds are able to pass into the prostate gland in sufficient quantities to achieve a cytotoxic effect on irradiation with low-energy neutrons. Further, prostate tumors, which are normally 5–15 cm from the skin surface, are typically readily accessible to a neutron beam.

Treatment of prostate cancer with BNCT should minimize significant blood loss, decrease morbidity, decrease incontinence, and decrease impotence as compared to traditional therapies. Further, tumors that extend beyond the margin of the prostate gland, which are difficult to remove surgically, can also be treated using this approach.

Presently, there is no recognized treatment for advanced renal cancer or advanced prostate cancer apart from hormonal manipulation. Chemotherapy and radiotherapy are not effective for advanced stages of these cancers. Further, patients who have only one kidney and who are suffering from renal cancer can only be treated surgically, leaving them enephric. BNCT of advanced renal and prostate cancer is an alternative therapy that is more effective than simple hormonal manipulation, chemotherapy, radiotherapy, or surgery.

Specific tumors that can be treated with this therapy include, but are not limited to, prostatic adenocarcinoma, renal cell carcinoma, and bladder carcinoma.

Any boron-containing compound that is sufficiently lipophilic to pass through the appropriate urogenital membranes in a quantity high enough to achieve therapy on irradiation with low-energy neutrons can be used, including any of those described in the Background of the Invention. If the compound is chiral, it is preferred to administer the compound in enantiomerically enriched form.

Carboranyl-containing nucleosides and oligonucleotides, which are lipophilic and have a high content of boron atoms, are particularly suited for use in BNCT of urogenital tumors. Preferred compounds include 5-carboranyl-2'-deoxyuridine (CDU) and 5-o-carboranyl-1-(2-deoxy-2-fluoro-β-D-arabinofuranosyl)uracil (CFAU). CDU is taken up by human lymphoma (CEM) and primary human peripheral blood mononuclear (PBM) cells and is intracellularly phosphorylated. The fact that CDU 5'-monophosphate is formed intracellularly indicates that the 5-o-carboranyl moiety is well tolerated and can mimic a pyrimidine nucleoside analogue. The entrapment of this molecule in cells allows for the enhancement of the tumor-to-blood ratio for BNCT. CFAU has increased glycosidic bond stability conferred by the β-fluorine group positioned on the 2'-carbon of the nucleoside.

Nonlimiting alternative compounds that can be used in BNCT of urogenital cancer are nucleosides that bear a (carboran-1-yl)phosphonate moiety in the 3' and/or 5'-position, dinucleotides and oligonucleotides that contain at least one uncharged 3',5'-O,O-[(carboran-1-yl-methyl)phosphonate] internucleotide linkage in place of the naturally occurring 3',5'-O,O-phosphodiester residue, or an oligonucleotide that bears a carboranyl-modified base in at least one of the nucleosides of the oligomer. In a preferred embodiment, the carboranyl-containing base is in a nucleoside located at the 3'-terminus, in the nucleoside adjacent to the 3'-terminal nucleoside, in the 5'-terminal nucleoside, or in the nucleoside adjacent to the 5'-terminal nucleoside. Oligonucleotides bearing carboranyl-containing bases in the 3'-terminal nucleoside or the nucleoside adjacent to the 3'-terminal are more resistant to degradation by 3'-exonucleases. It has been discovered that olignucleotides bearing carboranyl-containing base units in the preferred positions hybridize more effectively to complementary nucleic acid sequences than oligonucleotides bearing carboranyl-containing bases in other positions.

In another embodiment of the invention, nucleosides and oligonucleotides bearing an -O-[(carboran-1-yl)alkyl]phosphate, S-[(carboran-1-yl)alkyl]phosphorothioate, or Se-[(carboran-1-yl)alkyl]phosphoroselenoate in place of the (carboran-1-yl)phosphonate moiety can be used.

Oligonucleotides can be designed for BNCT of urogenital cancers according to methods described herein that are complementary to overexpressed or unique RNA or DNA sequences in target urogenital tumor cells, as a means to selectively accumulate the boron-containing material into these cells. Oligonucleotides of specific gene sequences that include one or more 3',5'-linking-(carboran-1-yl)phosphonate moieties can also be used in antisense therapy in the selective modification of gene expression.

Compounds can be used in urogenital BNCT therapy that contain boron clusters as a means to enhance lipophilicity wherein the boron is not enriched in $^{10}B$, but instead, in the $^{11}B$ isotope. The compounds should be enriched with a suitable amount of $^{10}B$ to achieve cytotoxicity, normally approximately 90–100% $^{10}B$ and typically between 92–96% $^{10}B$.

Other families of compounds that can be used to achieve BNCT of urogenital cancers include, but are not limited to, hydroxyalkylated carboranes, organoboronic acids, and boron-modified organic compounds such as amino acids, antibodies, antigens, proteins, peptides (including carboranylpeptides), carbohydrates (including glycosyl carboranes), polysaccharides, lipids, L- and D-nucleosides, nucleoproteins, lipoproteins, synthetic polypeptides, oligonucleotides, porphyrins, and drugs. The term drug, as used herein, refers to any substance used internally or externally as a medicine for the treatment, cure, prevention or diagnosis of a disease or disorder.

The therapy is accomplished by administering the boron-containing compound by any appropriate route, including by intravenous injection, oral delivery or by catheter or other direct means, in such a manner that the compound accumulates in the target tumor. Preferably, the compound concentrates in the tumor prior to irradiation, and advantageously, in a ratio of approximately or 2:1, or at least approximately 1.5:1 tumor:blood prior to irradiation. The boron-containing compound can be administered once or serially. After desired accumulation of the compound in the tumor, the site is irradiated with an effective amount of low energy neutrons. The site can be irradiated through the skin, or alternatively, the site can be totally or partially exposed prior to irradiation. Administration of the boron-containing compound followed by irradiation can be repeated as necessary. If desired, the tumor is removed to the extent possible surgically, and then the remaining tumor is destroyed using methods described herein.

In an alternative embodiment, the patient is dosed with an appropriate amount of the boron-containing compound, and irradiated with an effective amount of $^{252}$Californium, a naturally-occurring neutron emitter, that is preferably inserted into the tumor, and then removed at an appropriate time.

BRIEF DESCRIPTION OF THE FIGURES

FIG. 5 is an illustration of a process for the preparation of 5-(o-carboranyl)-5'-O-dimethoxytrityl-2'-O-deoxyuridine-3'-(N,N-diisopropyl-β-cyanoethyl)phosphoramidite.

FIG. 6 is an illustration of the chemical structures of a $B_xH_{10}$ carborane moiety and the anionic o-nido-7,8-$C_2B_9H_{(11\ or\ 12)}$ and o-closo-1,2-$C_2B_{10}H_{12}$ forms of carborane.

DETAILED DESCRIPTION OF THE INVENTION

Figure 1:
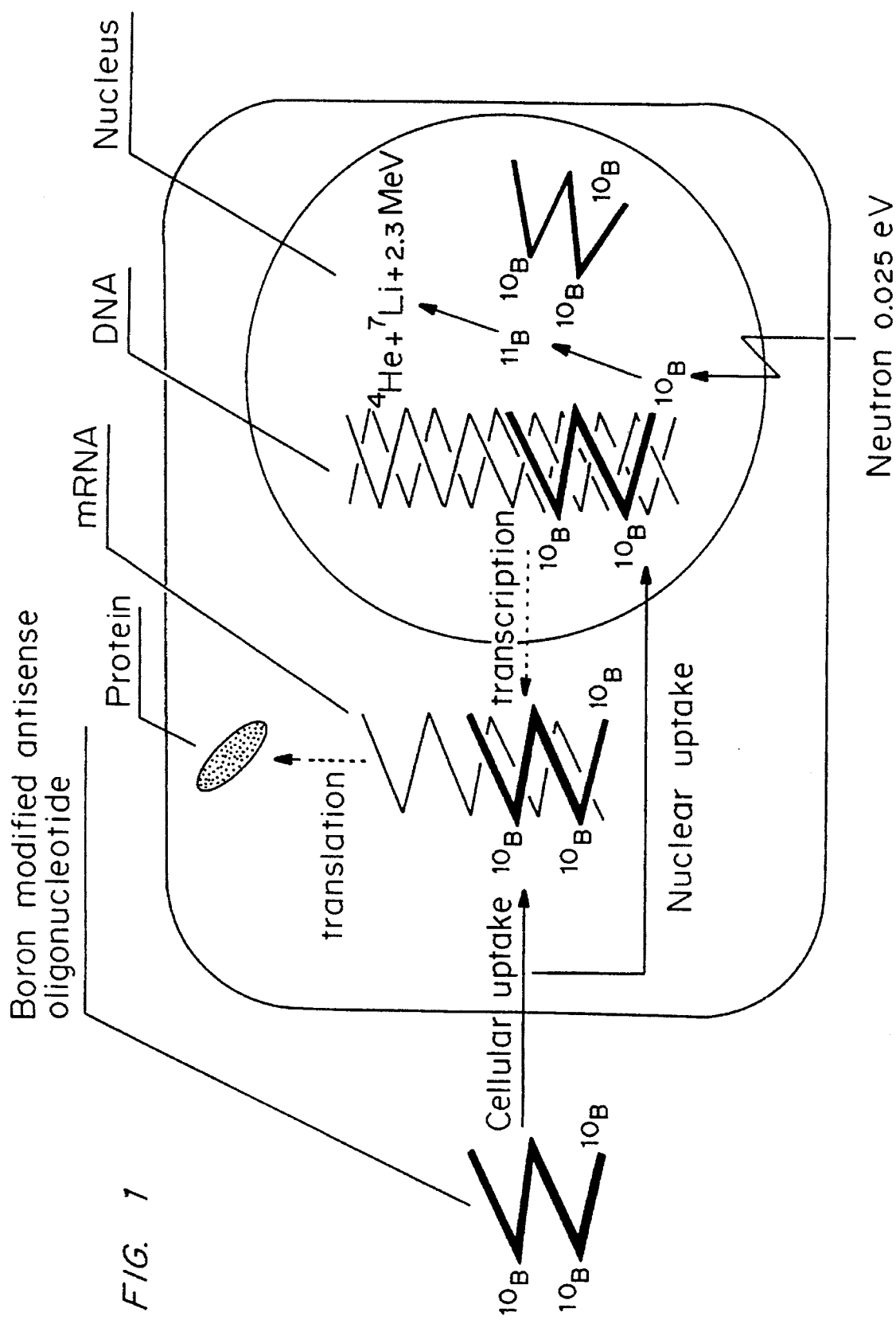
FIG. 1 is a schematic illustration of a hypothetical mechanism of action of boronated oligonucleotides for BNCT.

The term alkyl, as used herein, unless otherwise specified, refers to a saturated straight, branched, or cyclic, primary, secondary, or tertiary hydrocarbon of $C_1$ to $C_{10}$, and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term lower alkyl, as used herein, and unless otherwise specified, refers to a $C_1$ to $C_4$ saturated straight or branched alkyl group.

The term alkylamino or arylamino refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term alkaryl or alkylaryl refers to an alkyl group with an aryl substituent.

The term aralkyl or arylalkyl refers to an aryl group with an alkyl substituent.

The term halo, as used herein, includes chloro, bromo, iodo, and fluoro.

The term purine or pyrimidine base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 6-azapyrimidine, including 6-azacytosine, 2- and/or 4-mercaptopyrimidine, uracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, acyl groups such as acetyl and propionyl, methanesulfonyl, and p-toluenesulfonyl.

The term heteroaryl or heteroaromatic, as used herein, refers to an aromatic moiety that includes at least one sulfur, oxygen, or nitrogen in the aromatic ring. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, pyridazinyl, pyrazinyl, cinnolinyl, phthalazinyl, quinoxalinyl, xanthinyl, hypoxanthinyl, and pteridinyl. Functional oxygen and nitrogen groups on the heterocyclic base can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl.

The term alkenyl, as referred to herein, and unless otherwise specified, refers to a straight, branched, hydrocarbon of $C_2$ to $C_{10}$ with-at least one double bond.

The term acyl refers to moiety of the formula —C(O)R', wherein R' is alkyl; aryl, alkaryl, aralkyl, heteroaromatic, alkoxyalkyl including methoxymethyl; arylalkyl including benzyl; aryloxyalkyl such as phenoxymethyl; aryl including phenyl optionally substituted with halogen, $C_1$ to $C_4$ alkyl or $C_1$ to $C_4$ alkoxy, or the residue of an amino acid.

The term enantiomerically enriched, as used herein, refers to a compound in which one enantiomer is present in excess, and preferably present to the extent of 95% or more, and more preferably 98% or more, including 100%.

The term oligonucleotide refers to an oligomer of thirty-five or less nucleotides linked through their 3' and 5'-hydroxyl or 2'- and 5'-hydroxyl groups.

The term amino acid includes naturally occurring and synthetic amino acids, and includes but is not limited to, alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, and histidinyl.

It should be understood that when the term (carboran-1-yl)phosphonate is used in this text, that -O-(carboran-1-yl)alkyl]phosphate, S-(carboran-1-yl)alkyl]phosphorothioate, or Se-(carboran-1-yl)alkyl]phosphoroselenoate can be used in place thereof.

Figure 7:
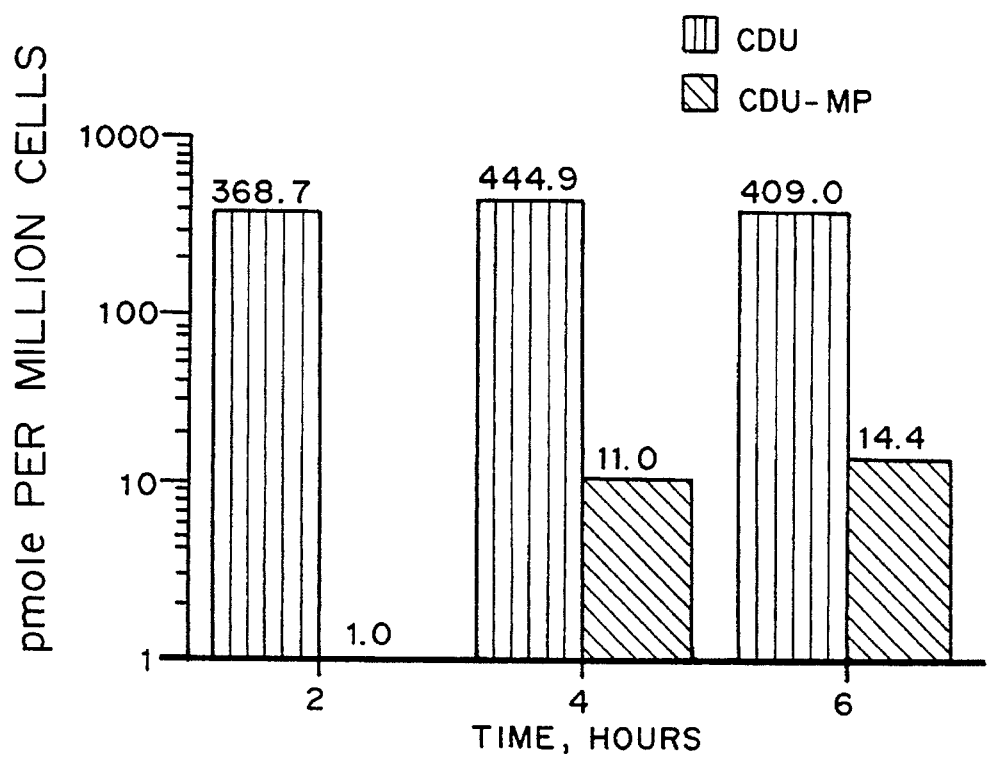
FIG. 7 is a bar chart graph of the uptake and phosphorylation of 1μM tritiated CDU in LNCaP cells (1,000 dpm/mol), as measured in pmole per million cells versus time in hours.
Figure 8:
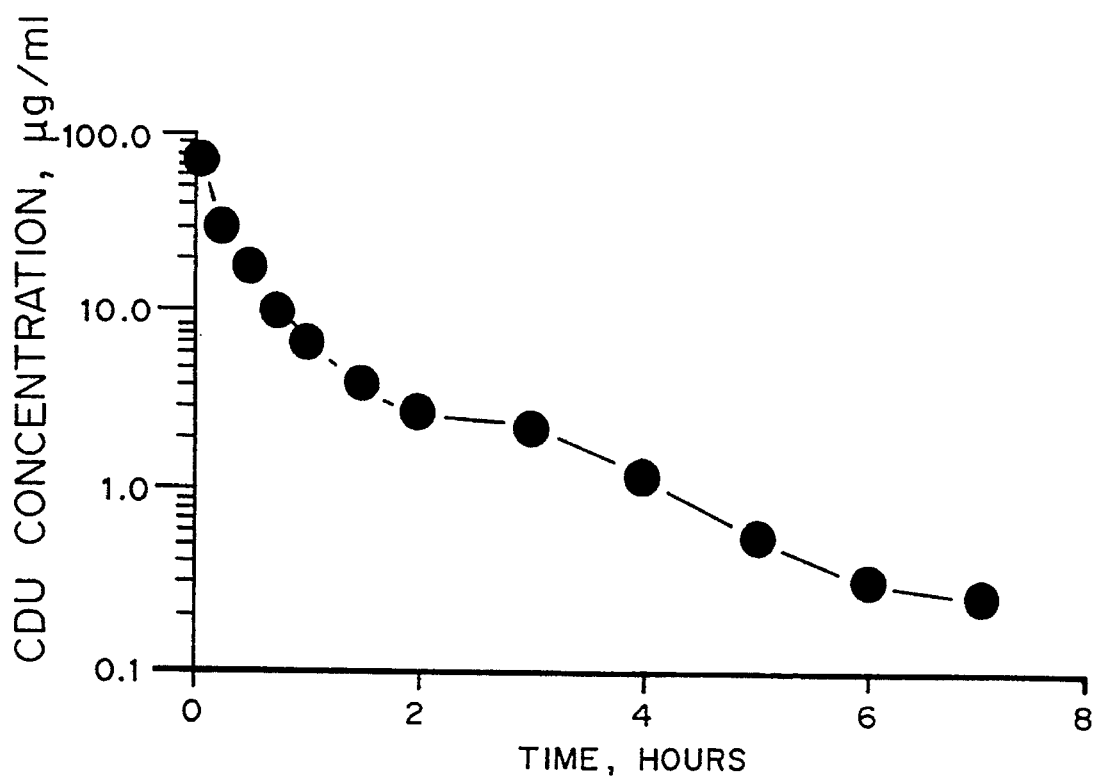
FIG. 8 is a graph of the mean (SE) plasma concentrations of CDU as a function of time following intravenous administration of a single dose of 25 mg/kg CDU to rats.

It has been discovered that boron neutron capture therapy, optionally combined with antisense oligonucleotide therapy, can be used in the treatment of urogenital cancer, and in particular, that of the prostate, bladder, and kidney. Any boron-containing compound that is sufficiently lipophilic to pass through the appropriate urogenital membranes in a quantity high enough to achieve therapy on irradiation with low-energy neutrons can be used. Carboranyl-containing nucleosides and oligonucleotides, which are lipophilic and have a high content of boron atoms, are particularly suited for use in BNCT of urogenital cancer. Preferred compounds include 5-carboranyl-2'-deoxyuridine (CDU) and 5-o-carboranyl-1-(2-deoxy-2-fluoro-β-D-arabinofuranosyl)uracil (CFAU). CDU is taken up by human lymphoma (CEM) and primary human peripheral blood mononuclear (PBM) cells and is intracellularly phosphorylated (FIG. 7). The fact that CDU-5'-monophosphate is formed intracellularly indicates that the 5-o-carboranyl moiety is well tolerated and can mimic a pyrimidine nucleoside analogue. The entrapment of this molecule in cells allows the enhancement of the tumor-to-blood ratio for BNCT. CFAU has increased glycosidic bond stability conferred by the β-fluorine group positioned on the 2'-carbon of the nucleoside.

In one embodiment, boron-containing oligonucleotides, and in particular, carboranyl-containing oligonucleotides, are targeted specifically to urogenital cancer cells to inhibit the overexpression of certain protooncogenes or to optimize expression of tumor suppressor genes which correlate well with clinical progression of tumors, including prostatic adenocarcinoma, renal carcinoma, and bladder carcinoma.

The lipophilicity of boron-modified compounds can be manipulated by the appropriate selection of the number and location of boron atoms in the molecule. For example, nucleosides, nucleotides, and oligonucleotides that bear one or more carboran-1-yl residues, allow for the concentrated and selective administration of boron to target cells. Lipophilicity can be manipulated by the appropriate selection of the number and location of the carboran-1-yl residues in the compound. In general, a carboranyl group linked directly to a phosphorus atom or through an appropriate spacer (such as alkyl or peptidyl) attached to oxygen, sulfur, or selenium, has a more significant effect on the lipophilicity of the compound than when the carboranyl group is attached in another location, such as on the base, because it acts as a substitute for a hydrophilic and ionizable hydroxy group.

I. Carboranyl Nucleosides and Nucleotides

A. The Carboranyl Moiety

Carboranes (also referred to as carbaboranes) are compounds that contain carbon atoms incorporated into a polyhedral borane. For a review of carborane chemistry, see F. Cotton and G. Wilkinson, *Advanced Inorganic Chemistry*, Fourth Edition, John Wiley and Sons, 318–320 (1980). The CH group is isoelectronic with $BH^-$, and thus can replace a $BH^-$ group. Polyhedral carboranes can thus be considered as formally derived from $B_nH_{n-2}$ ions, with two carbon replacements, leading to molecules of the general formula $B_{n-2}C_2H_n$. Neutral two carbon carboranes are generally of the formula $B_nC_2H_{n+2}$, wherein n is 3–10. For the purposes described herein, while any of these carboranes in any isomeric form can be used, carboranes wherein n=9 or 10 are preferred.

When the two carbon atoms are next to each other in the carborane framework, the carborane is referred to as a 1,2- or ortho-carborane (o-carborane). For example, $B_{10}C_2H_{12}$ is usually prepared as a 1,2-isomer, which when heated rearranges to a 1,7-isomer.

Carboranes can exist in a number of isomeric forms. "Closo" carboranes are closed cage structures, whereas "nido" carboranes are open nest-like structures. Examples are anionic o-nido-7,8-$C_2B_9H_{(11\ or\ 12)}$ and neutral o-closo-1,2-$C_2B_{10}H_{12}$. Carboranes can also exist as one of four arachno isomers or as a hypho-isomer. Both the 1,2- and the 1,7-dicarbadodecaboranes and their C-substituted derivatives, on treatment with strong base, are degraded with loss of boron to give isomeric nido-carborane anions, $B_9C_2H_{(11\ or\ 12)}$. Both isomeric $B_9C_2H_{(11\ or\ 12)}$ ions on treatment with anhydrous acid followed by heating are converted into the closo-carborane $B_9C_2H_{11}$.

Carboranes are typically prepared by the interaction of boranes or borane adducts with acetylenes. The most common carboranes are $B_{10}C_2H_{12}$ and its carbon-substituted derivatives. Carbon-substituted carboranes can be prepared with substituted acetylenes, as known to those skilled in the art, or, for example, by reaction of the carbaborane with a strong base to replace a hydrogen with lithium, followed by treatment with a desired electrophilic reagent. Acetylene derivatives that can be used to provide substituted carborane moieties are described, for example, in Heying, T. L., et al., *Inorganic Chemistry*, 2(6) 1089–1092 (1963).

Anions, such as anionic carboranes, can be administered as pharmaceutically acceptable salts of a single or multivalent pharmaceutically acceptable cation, including but not limited to, zinc, calcium, bismuth, barium, magnesium, aluminum, copper, cobalt, nickel, cadmium, sodium, potassium, pyridinium, quaternary amine, ammonium, protonated ethylenediamine, or protonated amino acids, including but not limited to protonated lysine and protonated arginine.

Carboranes can be incorporated into any selected carrier molecule to provide an agent for BNCT, including but not limited to amino acids, proteins, peptides, carbohydrates, polysaccharides, lipids, nucleoproteins, lipoproteins, synthetic polypeptides, porphyrins, oligonucleotides, including antisense oligonucleotides, DNA-intercalators, or drugs.

B. Carboranyl Nucleosides and Nucleotides i) Carboranyl-containing Nucleosides and Nucleotides In one embodiment, BNCT is carried out using a carboranyl-containing nucleoside or nucleotide. The carborane moiety can be located in any appropriate location on the molecule. Methods for the synthesis of carboranyl-containing nucleosides and nucleotides are well known to those of ordinary skill in the art, and are described, for example, in references listed in the Background of the Invention.

Nonlimiting examples of carboranyl containing bases that can be used in carboranyl-containing nucleosides or nucleotides are illustrated in Formulas I through VI.

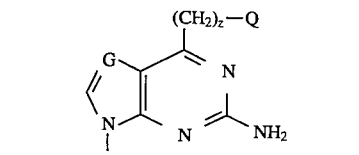

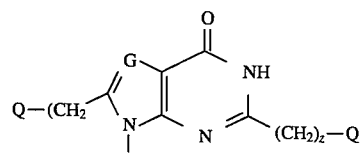

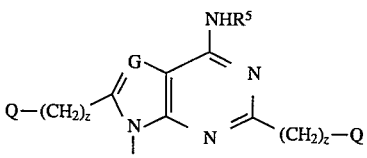

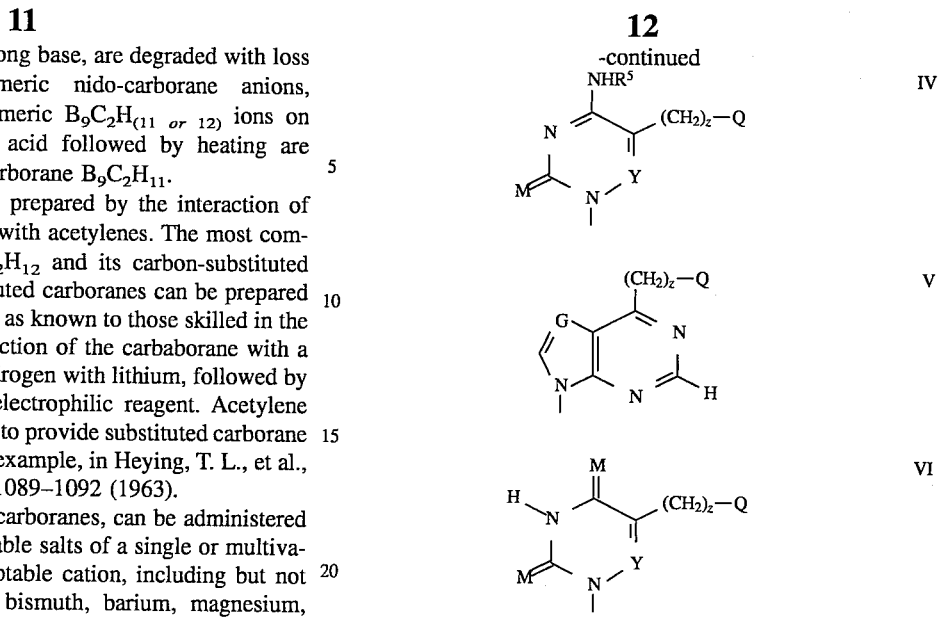

wherein:

Q is a carboranyl group such as $B_{10}H_{10}C_2R_4$, wherein $R_4$ is —H, —OH, —CH$_2$OH, —CH$_2$X (wherein X is halogen) or —$B_9C_2H_{(11\ or\ 12)}$ (a nido-carborane anion);

$R^5$ is lower alkyl;

G is N or CH;

M is O, S, or Se;

Y is CH or N; and z is 0 to 5.

Nonlimiting examples of the carbohydrate moieties of the nucleosides and nucleotides include those of the following formula.

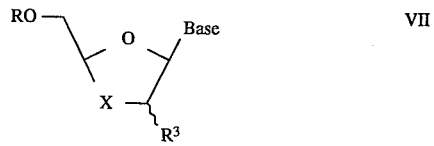

wherein: $R^3$ is hydroxyl, hydrogen, halogen, —CN, —N$_3$, lower alkyl, alkylamino, dialkylamino, alkoxy; and wherein the $R^3$ group can be in the ribosyl ("down" with respect to the sugar moiety when orienting the ring such that the oxygen is in the back) or the arabinosyl ("up") conformation;

X is O, S, Se, S(O), S(O)$_2$, CH$_2$, or CHR$_3$;

R is hydrogen, monophosphate, diphosphate, triphosphate, alkyl, or acyl, and the base is any purine or pyrimidine.

Particularly useful compounds include 5-carboranyl-2'-deoxyuridine (CDU), 5-o-carboranyl-1-(2-deoxy-2-fluoro-β-D-arabinofuranosyl)uracil (CFAU), 5-carboranyl-1-(β-D-xylofuranosyl)uracil, boronated derivatives of 2',3'-dideoxy-3'-thianucleosides, including 5-carboranyl-2',3'-dideoxy-3'-thiacytidine, and boronated derivatives of 2',3'-dideoxy-3'-oxanucleosides, including 5-carboranyl-2',3'-dideoxy-3'-oxacytidine. Other useful compounds include boronated L-nucleosides, for example, 5-carboranyl-L-2',3'-dideoxycytidine (5-carboranyl-L-DDC), and carboranyl-β-D-dioxolanyl purine nucleosides of the formula

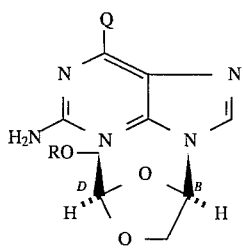

In another embodiment, boron-containing compounds (see U.S. Ser. No. 07/840,093, now allowed, which corresponds to PCT WO 93/17028) are used of the formulae:

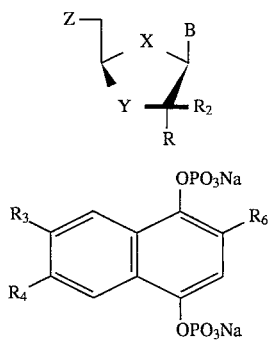

wherein: Z is OH, —OP(=O)(OH)$_2$, —OP(=O)(OH)OP(=O)(OH)$_2$, —OP(=O)(OH)OP(=O)(OH)OP(=O)(OH)$_2$, OR$_5$ (wherein R$_5$ is a hydroxy protecting group such as tri-C$_{1-4}$-alkylsilyl, di-C$_{1-4}$-alkyl-phenylsilyl, C$_{1-4}$-alkyl-diphenylsilyl, or trityl), —P(=O)(OH)$_2$, —P(=O)(OR$_6$)$_2$ (wherein R$_6$ is C$_{1-4}$-alkyl), —OR$_6$, R$_6$NH—, R$_6$R$_6$N—, R$_6$C(=O)O—, —SH, or —SR$_6$;

X is O, S, NR' (wherein R' is H or C$_{1-4}$-alkyl) or CHR';

Y is O, S, NR' or CHR' (wherein R' has the same meaning given above);

R$_1$ and R$_2$ are each, independently, H, C$_{1-4}$-alkyl, —CF$_3$, or —F;

B=a purine or pyrimidine base as described above, or selected from the group consisting of:

wherein Q is a carboranyl group such as —B$_{10}$H$_{10}$C$_2$R$_8$, wherein R$_8$ is —H, —OH, —CH$_2$OH, —CH$_2$X (wherein X is F, Cl, Br, I) or —B$_9$C$_2$H$_{12}$ nidocarborane anion)

R$_7$ is C$_{1-4}$-alkyl or H;

W is N or CH; and

R$_3$ and R$_4$ are each, independently, —H, —B(OH)$_2$, —B(OR$_6$)$_2$, or a carboranyl group having the formula —B$_{10}$H$_{10}$C$_2$R$_8$, wherein R$_8$ is —H, —OH, —CH$_2$OH, —CH$_2$X (wherein X is F, Cl, Br, I) or —B$_9$C$_2$H$_{12}$ (nidocarborane anion) provided that one of R$_3$ and R$_4$ is —H and the other of R$_3$ and R$_4$ is not —H.

ii). Nucleosides with (carboran-1-yl-methyl)phosphonate in the 3' or 5'-position, or both In another embodiment, a nucleoside is provided for BNCT of urogenital cancer that contains an (carboran-1-yl-methyl)phosphonate in the 3' or 5'-position of the molecule. Nonlimiting examples are the nucleosides of Formulas VIII, IX, and X illustrated below:

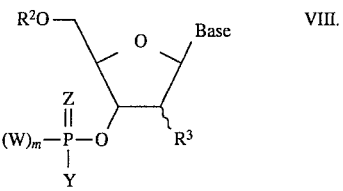

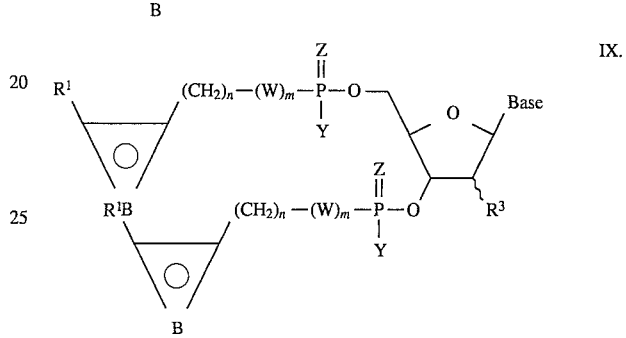

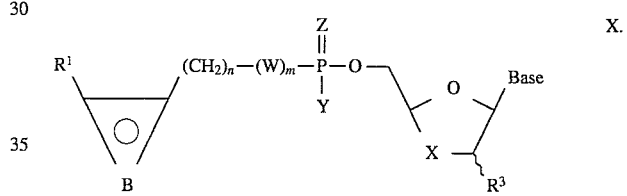

wherein:

R$^1$ is alkyl, haloalkyl, alkenyl, alkoxyalkyl, aryl, heteroaryl, trifluoromethyl, alkylaryl, arylalkyl, or halogen;

R$^2$ is hydrogen, alkyl, acyl (including acetyl); sulfonate ester including alkyl or arylalkyl sulfonyl including methanesulfonyl; a mono, di or triphosphate ester; trityl or monomethoxytrityl; benzyl, wherein the phenyl group is optionally substituted with one or more substituents as described in the definition of aryl given above; silyl, including trialkylsilyl (such as t-butyldimethylsilyl) or diphenylmethylsilyl; lipid; peptide; or cholesterol;

R$^3$ is hydroxyl, hydrogen, halogen, —CN, —N$_3$, lower alkyl, amino, alkylamino, dialkylamino, alkoxy; and wherein the R$^3$ group can be in the ribosyl ("down" with respect to the sugar moiety when orienting the ring such that the oxygen is in the back) or the arabinosyl ("up") conformation;

B represents the boron moiety of a carboranyl group, and specifically includes anionic o-nido-7,8-C$_2$B$_9$H$_{(11 \text{ or } 12)}$ and neutral o-closo-1,2-C$_2$B$_{10}$H$_{12}$;

W is O, S, or Se;

X is O, S, S(O), S(O)$_2$, CH$_2$, or CHR$^3$;

Y is OH, SH, SeH, or halogen, and in particular, fluorine;

z is O or S n is 1–5; and m is 0 or 1.

The base is preferably a purine or pyrimidine base as defined above, and preferably is thymine, uracil, 5-halouracil including 5-fluorouracil, cytosine, 5-halocytosine including 5-fluorocytosine, adenine, guanine, 2,6-diaminopurine, 2-amino-6-chloropurine, 6-aza-pyrimidine (including 6-azacytidine), 2-aminopurine, 5-lower alkyl uracil, or 5-lower alkylcytosine, 2-thiouracil, 2,4-thiouracil, 4-thiouracil, 6-chloropurine, 5-carboranyluracil, 5-carboranylcytosine and other carboranylpurines and carboranylpyrimidines, including those described above.

iii). Dinucleotides containing an uncharged 3',5'-O,O-[(carboran-1-yl-methyl)phosphonate]internucleotide linkage In a third embodiment, a dinucleotide is provided for BNCT of urogenital cancer wherein two nucleosides are connected via an uncharged 3',5'-O,O-[(carboran-1-yl-methyl)phosphonate] linkage. Nonlimiting examples are compounds of Formulas XI and XII.

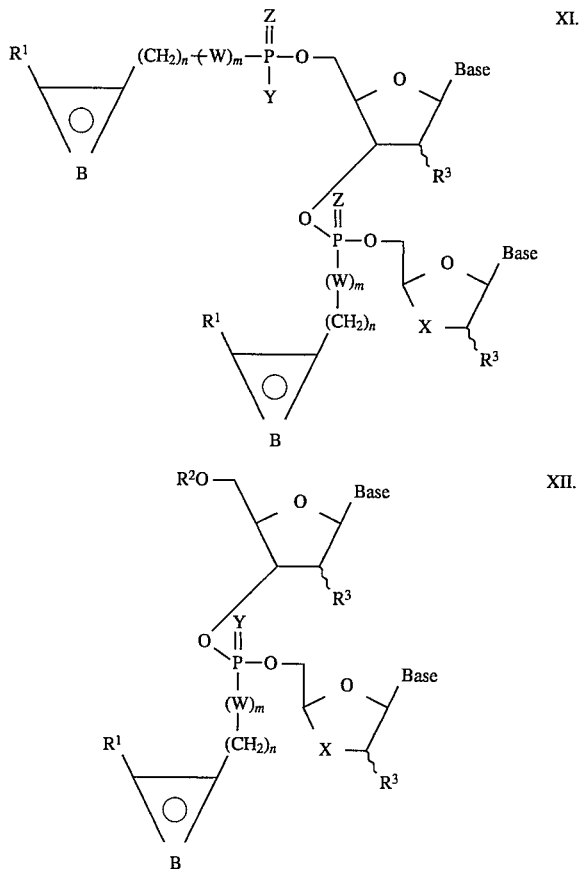

wherein $R^1$, $R^2$, $R^3$, B, W, X, Y, Z, m and n are as defined above.

iv). Oligonucleotides containing an uncharged 3',5'-O,O-[(carboran-1-yl-methyl)phosphonate] internucleotide linkage In a fourth embodiment, oligonucleotides and phosphothioate or dithioate oligonucleotides, methylphosphonate oligonucleotides, and dephosphooligonucleotides (such as peptido-oligonucleotides) are provided for BNCT of urogenital cancer, optionally in combination with AOT that contain at least one 3',5'-O,O-[(carboran-1-yl-methyl)phosphonate] internucleotide linkage. The 3',5'-O,O-[(carboran-1-yl-methyl)phosphonate can link the terminal two nucleotides at the 3'-end of the oligonucleotide, the terminal two nucleotides at the 5'-end of the oligonucleotide, or, alternatively, two nucleotides in the internal section of the oligonucleotide, including adjacent ones. In light of the fact that most oligonucleotides are degraded by 3'-exonucleases, in a preferred embodiment, an oligonucleotide is provided wherein a 3',5'-O,O-[(carboran-1-yl-methyl)phosphonate links at least the terminal two nucleotides at the 3'-terminus or the nucleosides adjacent to these.

The oligonucleotide, if desired, can contain more than one 3',5'-O,O-[(carboran-1-yl-methyl)phosphonate linkage, up to a fully modified oligonucleotide. In a preferred embodiment, the oligonucleotide has between approximately one and five modified linkages for a typical (thirty or less)-mer.

Any of the purine or pyrimidine bases defined above can be used in the oligonucleotide, in any appropriate sequence, as discussed in more detail below. In one embodiment, naturally occurring nucleosides, such as adenosine, guanosine, cytidine, thymidine, or uridine, are present in the oligonucleotide.

A nucleotide can be used as the 3'-terminus that contains an X moiety, wherein X is as defined above, and preferably, O or S.

Synthetic oligonucleotides with 3',5'-O,O-[(carboran-1-yl-methyl)phosphonate] linkages of specific sequences can be prepared for hybridization to a complementary nucleic acid sequence to inhibit transcription or replication (if the target sequence is DNA) inhibit translation (if the target sequence is RNA), or to inhibit processing (if the target sequence is pre-RNA). Antisense carboranyl-modified oligonucleotides can be prepared, for example, that inhibit protein biosynthesis by hybridization to a target mRNA sequence, and for other purposes.

Carboranyl-containing oligonucleotides can also be prepared that hybridize to a specific gene sequence in double stranded DNA to form a triple stranded complex (triplex) that inhibits the expression of that gene sequence.

A wide variety of nucleic acid sequences with known function have been reported, and given the extensive research currently being conducted in this area, many others will be reported in the future. Given the disclosure herein, one of ordinary skill in the art can prepare any nucleic acid sequence modified as desired with one or more 3',5'-O,O-[(carboran-1-yl-methyl)phosphonate] linkages for use in BCNT or AOT of urogenital cancer. It should be understood that this invention is not directed to specific nucleic acid sequences, but instead is a general technique to increase the stability, lipophilicity, transportability, and boron concentration of a sequence of interest.

v). Oligonucleotides with carboranyl moiety in the base

In a fifth embodiment, oligonucleotides for BNCT of urogenital cancer, optionally in combination with AOT, are provided that contain a carboranyl moiety in a base unit of one of the nucleotides. Nonlimiting examples of carboranyl containing bases are illustrated above (Formulas I through VI).

The carboranyl-containing base can be in a 3'- or 5'-terminal nucleotide, in a nucleotide adjacent to the 3'- or 5'-terminal nucleoside, or in an internal nucleotide. It has been discovered that oligonucleotides that contain carboranyl-modified bases in the 3'- or 5'-terminal nucleotide or in a nucleotide adjacent to the 3'- or 5'-terminal nucleoside hybridize more effectively to complementary nucleic acid sequences than oligonucleotides that bear carboranyl-containing bases in internal nucleotides. It has also been discovered that oligonucleotides that contain carboranyl-modified bases in the 3'-terminal nucleotide, in a nucleotide adjacent to the 3'-terminal nucleoside, or in both the 3'-terminal and 5'-terminal nucleosides are more resistant to degradation than those otherwise modified.

As discussed above, it should be understood that any nucleic acid sequence of interest can be modified by addition of a carboranyl moiety to a base unit in the oligomer. This invention is not directed to specific nucleic acid sequences, but instead is a general technique.

vi). Oligonucleotides with both a 3',5'-O,O-[(carboran-1-yl-methyl)phosphonate] internucleotide linkage and a carboranyl-containing base In a sixth embodiment, oligonucleotides are provided for BNCT of urogenital cancer, optionally in combination with AOT, that contain both a 3',5'-O,O-[(carboran-1-yl-methyl)phosphonate] internucleotide linkage and a carboranyl-containing base. The carboranyl-containing base can be on the same or different nucleotide than that linked via a 3',5'-O,O-[(carboran-1-yl-methyl)phosphonate] bridge.

C. Stereochemistry and Enantiomerism

A boron-containing compound should be selected that has a stereochemistry that optimizes its utility as an agent for BNCT and AOT of urogenital cancer. The stereochemistry of the nucleotides and oligonucleotides presented herein is influenced by the configuration of the nucleosides and the configuration of the chiral (carboran-1-yl-methyl)phosphonate moiety, if present in the compound.

Stereochemistry of Nucleosides

In one embodiment, the oligonucleotides of the present invention are comprised of naturally occurring nucleosides, preferably adenosine, guanosine, cytidine, thymidine, and uridine that have been modified by addition of a 3',5'-O,O-[(carboran-1-yl-methyl)phosphonate] linkage or by addition of a carboranyl moiety to one or more of the base units. The naturally occurring nucleosides have one stereochemical configuration that is set by nature. However, if a nonnaturally occurring nucleoside is used in a oligonucleotide or alone, stereochemical issues become relevant. Since the 1' and 4' carbons of the sugar or modified sugar moiety (referred to below generically as the sugar moiety) of the synthetic nucleosides are chiral, their nonhydrogen substituents ($CH_2OR^2$ and the pyrimidine or purine base, respectively) can be either cis (on the same side) or trans (on opposite sides) with respect to the sugar ring system. The four optical isomers therefore are represented by the following configurations (when orienting the sugar moiety in a horizontal plane such that the "primary" oxygen (that between the C1' and C4'-atoms) is in back): cis (with both groups "up", which corresponds to the configuration of naturally occurring nucleosides), cis (with both groups "down", which is a nonnaturally occurring configuration), trans (with the C1' substituent "up" and the C4' substituent "down"), and trans (with the C1' substituent "down" and the C4' substituent "up"). In general, "D-nucleosides" are cis nucleosides in a natural configuration and the "L-nucleosides" are cis nucleosides in the nonnaturally occurring configuration.

According to the present invention, synthetic nucleosides can be used in oligonucleotides or alone in any of these configurations. It is known that certain synthetic nucleosides can be more active, or less toxic, or both, in one configuration than in other configurations. One of ordinary skill in the art given this disclosure can easily determine the optimal stereochemical configuration for a specific synthetic nucleoside for a desired application. Alternatively, the nucleoside can be used as a racemic mixture or in the form of an enantiomerically enriched composition.

Enzymatic methods for the separation of D and L enantiomers of cis-nucleosides are disclosed in, for example, Nucleosides and Nucleotides, 12(2), 225–236 (1993); European Patent Application Nos. 92304551.2 and 92304552.0 filed by Biochem Pharma, Inc.; and PCT Publication Nos. WO 91/11186, WO 92/14729, and WO 92/14743 filed by Emory University.

Separation of the acylated or alkylated racemic mixtures of D and L enantiomers of cis-nucleosides can also be accomplished by high performance liquid chromatography with chiral stationary phases, as disclosed in PCT Publication No. WO 92/14729.

α and β-L-Nucleosides can be prepared from methods disclosed in, or standard modifications of methods disclosed in, for example, the following publications: Jeong, et al., *J. of Med. Chem.*, 36:182–195 (1993); European Patent Application Publication No. 0 285 884; Génu-Dellac, C., G. Gosselin, A.-M. Aubertin, G. Obert, A. Kirn, and J.-L. Imbach, "3-substituted thymine α-L-nucleoside derivatives as potential antiviral agents; synthesis and biological evaluation," *Antiviral Chem. Chemother.*, 2:83–92 (1991); Johansson, K. N. G., B. G. Lindborg, and R. Noreen, European Patent Application 352 248; Mansuri, M. M., V. Farina, J. E. Starrett, D. A. Benigni, V. Brankovan, and J. C. Martin, "Preparation of the Geometric isomers of DDC, DDA, D4C and D4T as potential anti-HIV agents," *Bioorg. Med. Chem. Lett.*, 1:65–68 (1991); Fujimori, So, N. Iwanami, Y. Hashimoto, and K. Shudo, "A convenient and stereoselective synthesis of 2'-deoxy-β-L-ribonucleosides, *Nucleosides & Nucleotides*, 11:341–349 (1992); Génu-Dellac, C., G. Gosselin, A.-M. Aubertin, G. Obert, A. Kirn, and J.-L. Imbach, "3-substituted thymine α-L-nucleoside derivatives as potential antiviral agents; synthesis and biological evaluation," *Antiviral Chem, Chemother.*, 2:83–92 (1991); Holy, A, "Synthesis of 2'-deoxy-L-uridine," *Tetrahedron Lett.*, 2:189–192 (1972); Holy, A., "Nucleic acid components and their analogs. CLIII. Preparation of 2'-deoxy-L-ribonucleosides of the pyrimidine series," *Collect Czech Chem. Commun.*, 37:4072–4087 (1992); Holy, A, "2'-deoxy-L-uridine: total synthesis of a Uracil 2'-deoxynucleoside from a sugar 2-aminooxazoline through a 2.2'-anhydronucleoside intermediate," In: Townsend LB, Tipson RS, ed. *Nucleic Acid Chem.*, 1:347–353 (Wiley, New York, 1992); Okabe, M., R.-C. Sun, S. Tan, L. Todaro, and D. L. Coffen, "Synthesis of the dideoxynucleosides ddC and CNT from glutamic acid, ribonolactone, and pyrimidine bases," *J. Org. Chem.*, 53:4780–4786 (1988); Robins, M. J., T. A. Khwja, and R. K. Robins, "Purine nucleosides. XXIX. Synthesis of 2'-deoxy-L-adenosine and 2'-deoxy-L-guanosine and their alpha anomers," *J. Org. Chem.*, 35:363–639 (1992); Génu-Dellac, C., Gosselin G., Aubertin A-M, Obert G., Kirn A., and Imbach J-L, "3'-substituted thymine α-L-nucleoside derivatives as potential antiviral agents; synthesis and biological evaluation," *Antiviral Chem. Chemother.*, 2(2):83–92 (1991); Génu-Dellac, C., Gosselin G., Imbach J-L; "Synthesis of New 2'-deoxy-3'-substituted-α-L-threo-pentofuranonucleosides of Thymine As a Potential Antiviral Agents," *Tetrahedron Lett.*, 32(1):79–82 (1991); Génu-Dellac, C., Gosselin G., Imbach J-L, "Preparation of New Acylated Derivatives of L-arabinofuranose and 2-deoxy-L-erythropentofuranose as Precursors for the Synthesis of L-pentofuranosyl nucleosides," 216:240–255 (1991); and Génu-Dellac, C., Gosselin G., Puech F., et al., "Systematic synthesis and antiviral evaluation of α-L-arabinofuranosyl and 2'-deoxy-α-L-erythropentofuranosyl nucleosides of the five naturally occurring nucleic acid bases," 10(b):1345–1376 (1991).

β-D-Nucleosides and racemic mixtures of synthetic nucleosides can be prepared as described in or by routine modifications or extensions of preparations described in numerous literature references, including but not limited to U.S. Pat. No. 4,916,122 to Chu, et al.; European Patent Application No. 0 217 580; PCT Application No. WO92/10497; Chu, C. K., et al., "A general synthetic method for 2',3'-dideoxynucleosides: total synthetic approach," *Nucleosides & Nucleotides*, 8:(5&6) 903–906 (1989); Chu, C. K., et al., "Enantiomeric synthesis of (+)-BCH-189 and (+)-1-β-D-5-(1,3-oxothiolanyl)cytosine from D-mannose and its anti-HIV activity," *J. Org. Chem.* (1991); Chu, C. K., et al., "Structure-activity relationships of pyrimidine nucleosides as antiviral agents for human immunodeficiency virus type 1 in peripheral blood mononuclear cells," *J. Med. Chem.*, 32:612 (1989); Huryn, D. M., et al., "Synthesis of iso-DDA, member of a novel class of anti-HIV agents," *Tetrahedron Lett.*, 30:6259–6262 (1989); Kreitsky, T. A., "3'-Amino-2',3'-dideoxyribonucleosides of some pyrimidines: synthesis and biological activities," *J. Med. Chem.*, 26:891–895 (1983); Lin, T., et al., "Synthesis and biological activity of various 3'-azido and 3'-amino analogues of 5-substituted pyrimidine deoxyribonucleosides," *J. Med. Chem.*, 26:1691–1696 (1983); Mansuri, M. M., et al., "Preparation of the geometric isomers of DDC, DDA, D4C and D4T as potential anti-HIV agents," *Bioorg. Med. Chem. Lett.*, 1:65–68 (1991); Okabe, M., et al., "Synthesis of the dideoxynucleosides ddC and CNT from glutamic acid, ribonolactone, and pyrimidine bases," *J. Org. Chem.*, 53:4780–4786 (1988); Peterson, M. L., "Synthesis and biological evaluation of 4-purinylpyrrolidine nucleosides," *J. Med. Chem.*, 34:2787–2797 (1991); Sterzycki, R. Z., et al., "Synthesis and anti-HIV activity of several 2'-fluoro-containing pyrimidine nucleosides," *J. Med. Chem.*, 33:2150–2157 (1990); Wilson, L. J., et al., "A general method for controlling glycosylation stereochemistry in the synthesis of 2'-deoxyribose nucleosides," *Tetrahedron Lett.* 1815 (1990); and Wilson, L. J., et al., "The synthesis and anti-HIV activity of pyrimidine dioxolanyl nucleosides," *Bioorg. Med. Chem. Lett.*, 3:(2) 169–174 (1993).

Stereochemistry at the Phosphorus Atom

Figure 3:
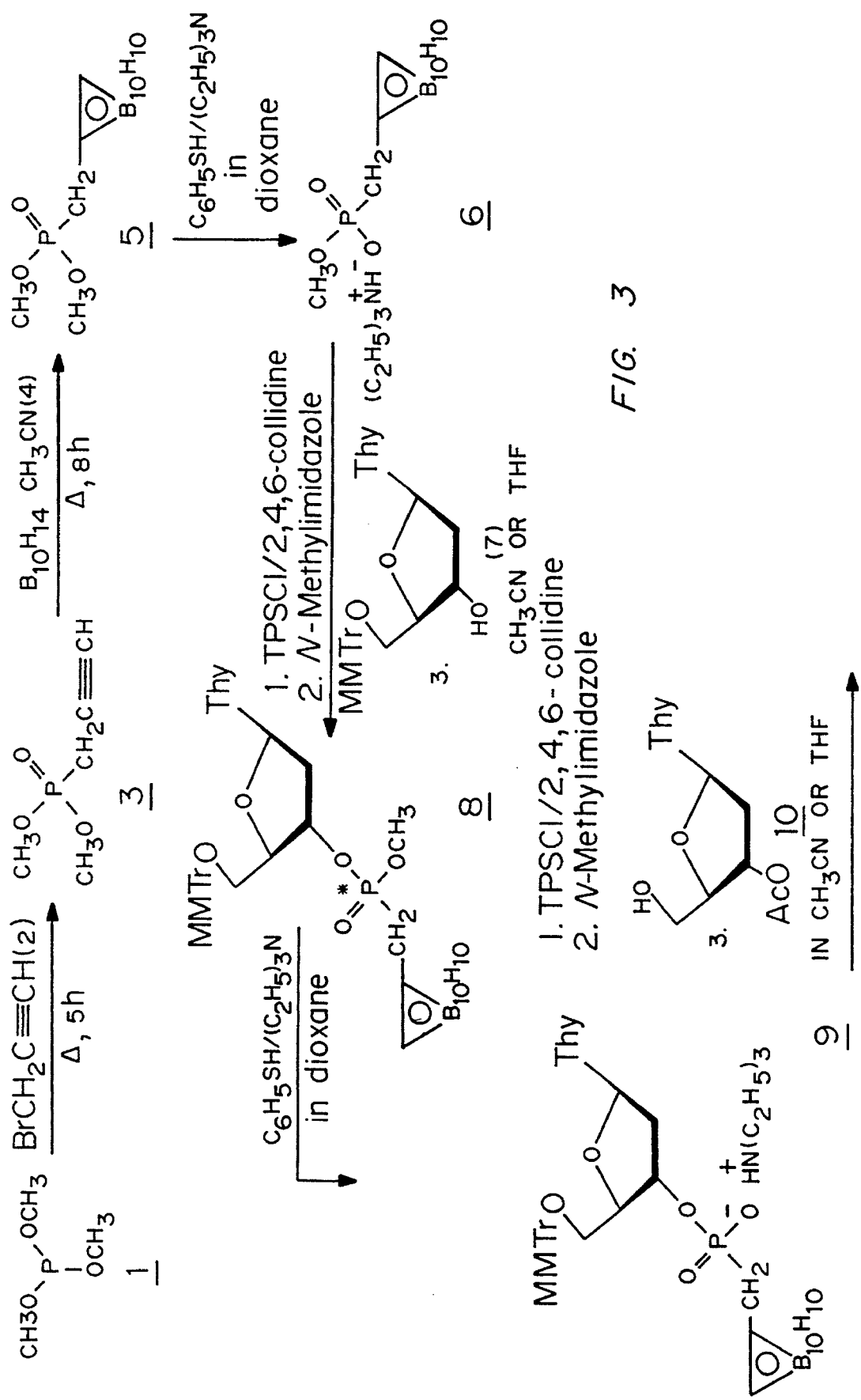
FIG. 3 is a schematic illustration of a process for the preparation of thymidine-(3',5')-thymidine(o-carboran-1-yl)methylphosphonate using the key starting material O-methyl(o-carboran-1-yl)methyl phosphonate.
Figure 3A:
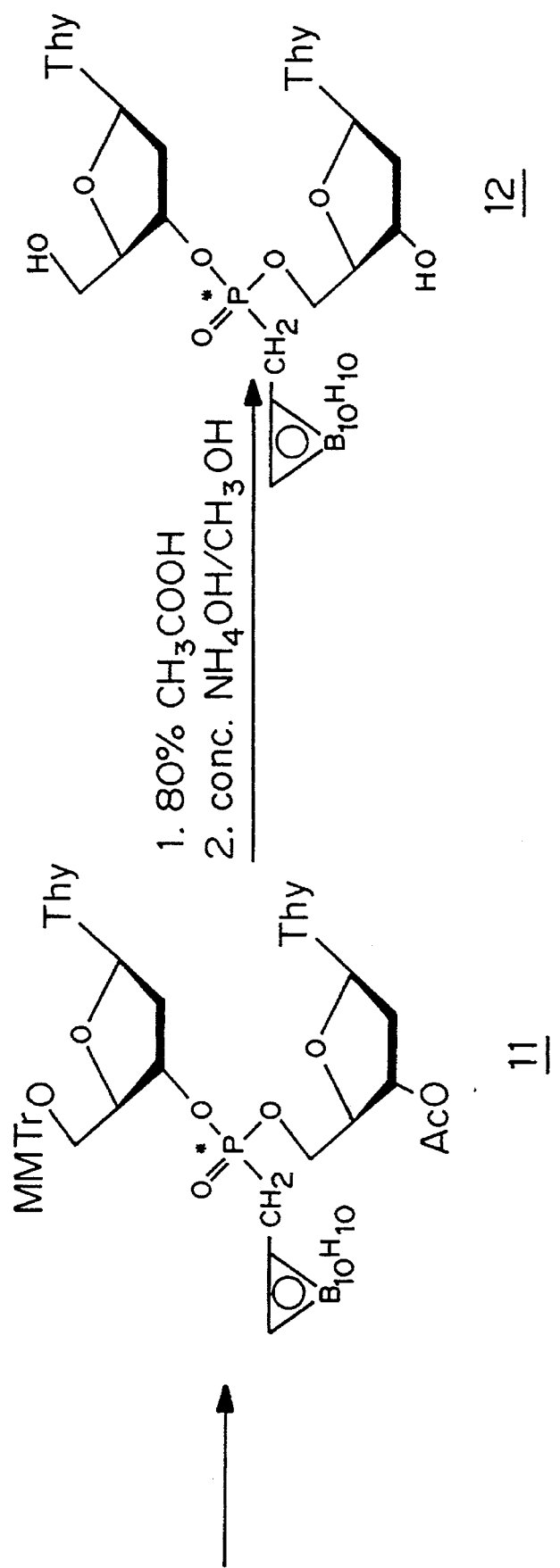

Replacement of one of the anionic prochiral oxygen atoms of phosphorus with a (carboran-1-yl)methyl moiety generates a center of chirality at the phosphorus atom (see, for example, compound 8, FIG. 3) and in nucleotides and oligonucleotides bearing this moiety (see, for example, compounds 11 and 12, FIG. 3). Due to this modification and the nonstereoselectivity of the coupling reaction described herein, the (carboran-1-yl)methylphosphonate oligonucleotide is typically obtained as a mixture of diastereoisomers.

For a process for the stereocontrolled synthesis of P-chiral oligonucleotides analogues, see Lesnikowski, *Bioorg. Chem.*, 21:127–155 (1993). Briefly, P-stereodefined, P-chiral oligonucleotides can be prepared using following methods.

(i) Enzymatic method. This approach is useful for the stereocontrolled synthesis of phosphorothioate and methylphosphonate oligonucleotide analogues.

(ii) Separation of diastereoisomeric oligonucleotides. This method is most useful for oligonucleotides containing up to three P-chiral internucleotide linkages (eight diastereoisomers).

(iii) Block synthesis: A dinucleotide is first synthesized as a mixture of diastereoisomers. In the second step the mixture is separated into individual diastereoisomeric species. Diastereoisomeric dinucleotides are next phosphorylated or phosphitylated and used as synthons in the synthesis of longer oligonucleotides. This method provides a method for the synthesis of oligonucleotides with stereodefined synthetic internucleotide links separated by natural or modified but not stereodefined internucletide links.

(iv) Stereospecific formation of internucleotide linkage: Diastereoisomerically pure monomers are first synthesized. Using diasteroisomerically pure monomers and a stereospecific coupling reaction P-stereoregular oligomers can be prepared.

(v) Stereospecific modification of internucleotide linkage.

The influence of absolute configuration at phosphorus of P-chiral antisense oligonucleotides on their physicochemical and biochemical properties has been studied. The absolute configuration at the phosphorus atom affects, among other things, solubility, transportability through cellular membranes, affinity toward complementary sequence of target nucleic acid (melting temperature), and resistance towards nucleolytic enzymes (Uhlman, et al., *Chem. Rev.*, 90:544–584 (1990)).

II. Methods for the Preparation of Carboranyl-Containing Nucleosides and Nucleotides A. Preparation of Carboranyl-Containing Nucleosides Methods for the preparation of carboranyl-containing nucleosides are known or can easily be adapted from known procedures. See generally, Goudgaon, N. M., El-Kattan, G. F., and Schinazi, R. F., "Boron containing pyrimidines, nucleosides, and oligonucleotides for neutron capture therapy," *Nucleosides & Nucleotides*, 13:849–880 (1994). A method for the preparation of CDU, for example, has been published in *Heteroatom Chem.*, 3:239–244 (1992). A working example for the preparation of CFAU is provided below.

EXAMPLE 1

Synthesis of CFAU

Melting points were determined on an Electrothermal IA 8100 digital melting point apparatus and are uncorrected. $^1$HNMR spectra were recorded on a General Electrix QE-300 (300 MHz) spectrometer. Mass spectrum analyses were performed using a PE-Sciex AP1 III LCMS with an electrospray interface (University of Alabama at Birmingham, Birmingham, Ala.) and on a VG Instruments 70-SE spectrometer (Emory University, Atlanta, Ga.). Experiments were monitored using TLC analysis performed on Kodak chromatogram sheets precoated with silica gel containing a fluorescent indicator, while column chromatography, employing silica gel (60–200 mesh; Fisher Scientific, Fair Lawn, N.J.), was used for the purification of products. Microanalyses were performed at Atlantic Microlabs Inc. (Atlanta, Ga.). Decaborane (purity >99%) was purchased from Boron Biologicals, Inc. (Raleigh, N.C.).

Figure 2:
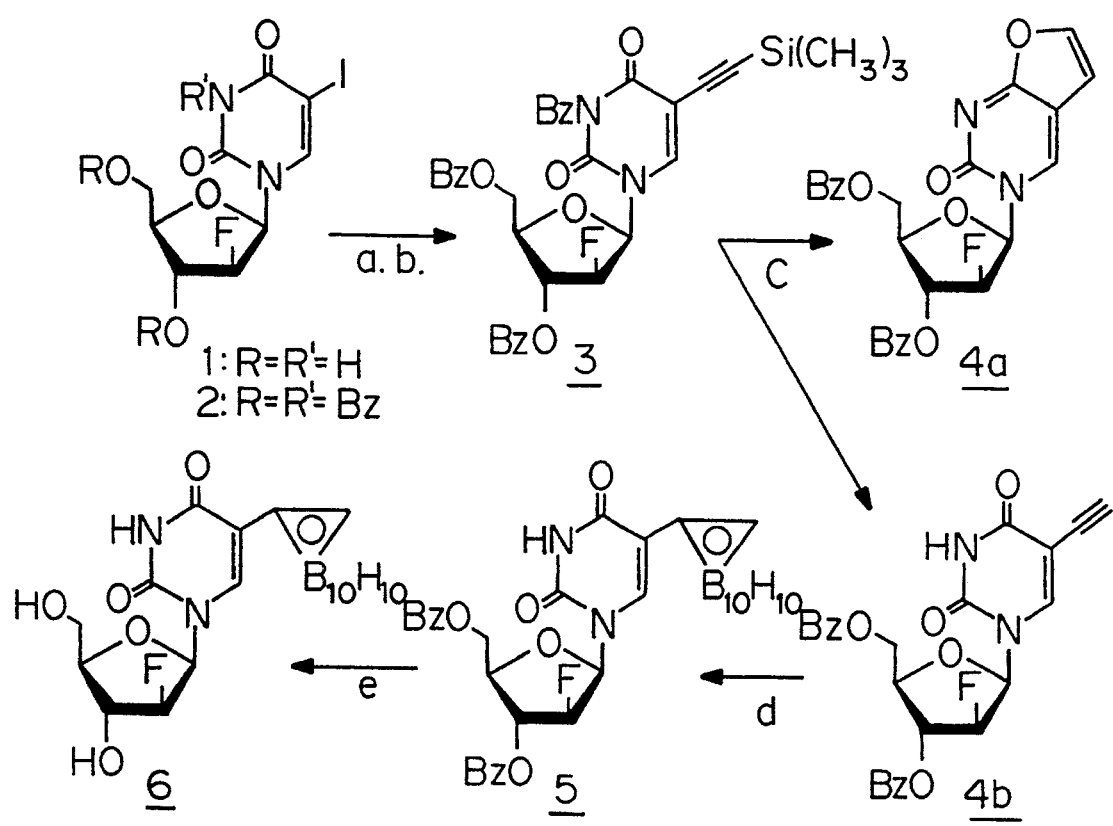
FIG. 2 is a schematic illustration of a process for the preparation of 5-o-carboranyl-1-(2-deoxy-2-fluoro-β-D-arabinofuranosyl)uracil (CFAU).

CFAU was synthesized using an adaptation of the methodology developed by Yamamoto, et al. (*J. Chem. Soc. Chem. Commun.*, 157–158 (1992)) (FIG. 2). 5-Iodo-1-(2-deoxy-2-fluoro-β-D-arabinofuranosyl)-uracil (FIAU) was first converted to its 3,3',5'-tri-N,O,O-benzoylated derivative with benzoyl chloride in pyridine. The fully protected 5-iodo nucleoside in dry THF was then coupled with (trimethylsily)acetylene in the presence of triethylamine at 50° C. using copper iodide and $(Ph_3P)_2PdCl_2$ as catalysts to give the 5-(trimethylsilyl)ethynyl-protected nucleoside. Removal of the TMS group was performed in THF using n-tetrabutylammonium fluoride. Under these conditions, cleavage of the $N^3$-benzoyl group occurred, leading to 5-ethynyl-1-(3, 5-di-O-benzoyl-2-deoxy-2-fluoro-β-D-arabinofuranosyl)uracil. The 5-alkynyl nucleoside was reacted with decaborane, as a bis(propionitrile) adduct, in refluxing toluene to yield the 5-o-carboranyl derivative. Deprotection of hydroxyl functions with methanolic sodium methoxide led to the desired compound CFAU. It should be noted that, under such basic conditions, it is possible to partially convert the closo-carboranyl nucleoside into its negatively charged nido-isomers. HPLC analysis of CFAU using a reverse phase C18 column and a gradient of acetonitrile in triethylammonium acetate buffer as the mobile phase indicated the present of less than 1% of the nido-CFAU derivatives, which are characteristically more polar than the closo-isomer.

CFAU was also synthesized de novo by performing a coupling reaction between 5-o-carboranyluracil and suitable protected 2-deoxy-2-fluoro-D-arabinofuranose. See *J. Med. Chem.*, 29:151–154 (1986). The rationale for this new synthesis is based upon the potentially broad accessibility of 5-o-carboranyl-modified nucleosides available by glycosylation of 5-o-carboranyluracil with natural or modified protected carbohydrates.

carboranylation of the base was the same as that described for the corresponding nucleoside and involved three main steps: such as alkynylation, deprotection, and decaborane insertion as the bis(propionitrile) adduct. The synthesis of 5-O-benzoyl-3-O-acetyl-2-deoxy-2-D-fluoroarabinofuranose was performed according to the known procedure. *Carbohydrate Research*, 42:233–240 (1975). The sugar derivative was then converted to its 1-bromo reactive form by bromination with HBr gas in $CH_2Cl_2$ at 0° C. The first coupling reaction was conducted in $CH_2Cl_2$ at room temperature between the silylated base and the 1-bromo carbohydrate derivative (Scheme 1). After 5 days, only traces of α,β-nucleosides were observed by TLC. When the same reaction was then performed using $ZnBr_2$ as catalyst, substantial amounts of two nucleosides were detectable after an overnight reaction. The separation of the anomeric mixture of protected nucleosides into the two pure diastereoisomers by column chromatography failed.

Therefore, the mixture of compounds was deblocked using NaOMe in MeOH at 0° C. α-CFAU (12) and β-CFAU (6) were separated by preparative thin-layer chromatography.

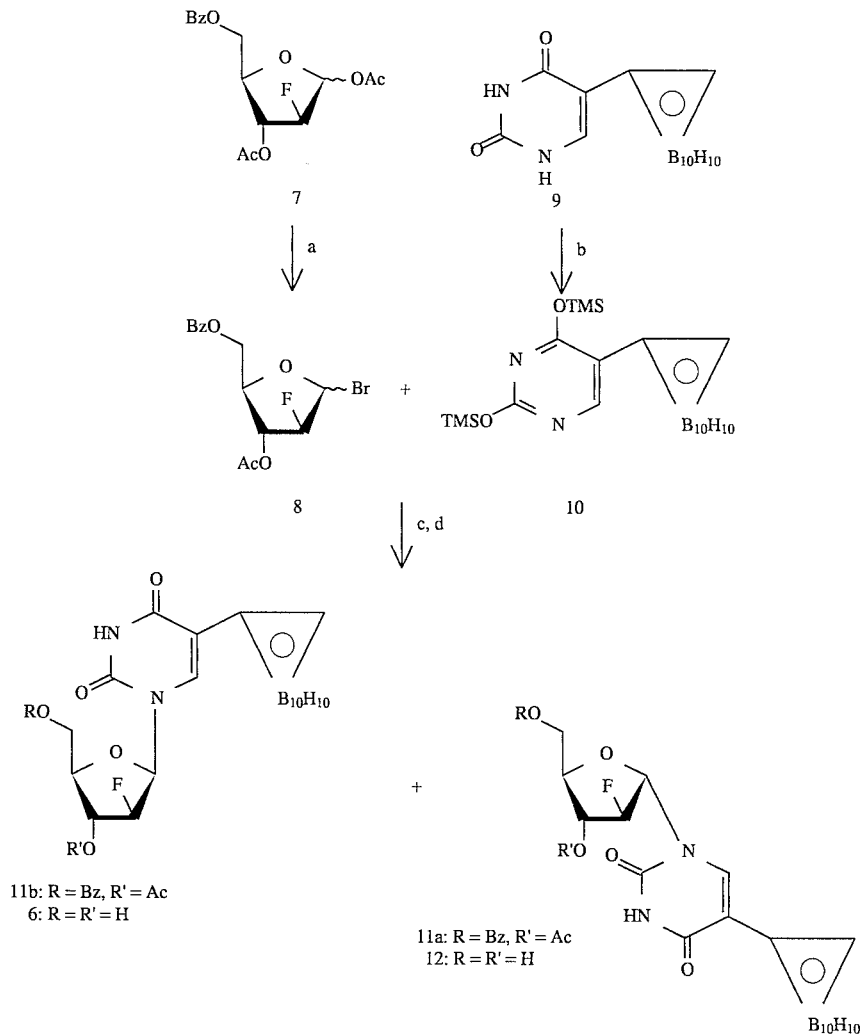

5-o-Carboranyluracil was synthesized in five steps from commercial 5-iodouracil. After conversion of 5-iodouracil to 2,4-dimethoxy-5-iodouracil, the procedure utilized for the

SCHEME 1

Synthesis of CFAU by Coupling Reaction 1-(3,5-Di-O-benzoyl-2-deoxy-2-fluoro-β-D-arabinofuranosyl)-$N^3$-benozyl-5-iodouracil. To a stirred solution of FIAU (2.23 g, 6 mmol) (1) in anhydrous pyridine (25 mL) was added benzoyl chloride (1.8 mL, 15 mmol) with stirring under an $N_2$ atmosphere. The reaction mixture was heated overnight at 50° C. The solution was cooled to room temperature and poured onto ice-water and the precipitate filtered. The crude product was chromatographed on a silica gel column using $CH_2Cl_2$ as eluant to yield the fully protected nucleoside 2 as a white powder (2.8 g, 69%): mp 186°–189° C.; $^1$H NMR ($CDCl_3$) δ4,56 (m, 1H, 4'-H), 4.85 (2dd, 2H, 5'-H, 5"-H), 5.29 (apparent dd, 1H, 2'-H, $J_{H2',F}$=50 Hz), 5.60 (apparent dd, 1H, 3'-H $J_{H3',F}$=19.4 Hz), 6.27 (dd, 1H, 1'-H, $J_{H1',F}$-23.8 Hz), 7.20–8.18 (m, 16H, aromatic protons, 6-H. Anal. ($C_{30}FH_{22}IN_2O_8$) C, H, N.

1-(3,5-Di-O-benzoyl-2-deoxy-2-fluoro-β-D-arabinofuranosyl)-$N^3$-benzoyl-5-[2-(trimethylsilyl)ethynyl]-uracil. The protected fluoronucleoside (2.6 g. 3.78 mmol), $(PPh_3)_2PdCl_2$ (265 Mg, 0.38 mmol), and CuI (144 mg, 0.76 mmol) were dissolved in anhydrous THF (38 mL). Triethylamine (1.6 mL, 11.3 mmol) and (trimethylsilyl)acetylene (1.1 mL, 7.56 mmol) were added under an argon atmosphere. The mixture was stirred at room temperature, and after 15 minutes, the solution turned dark. The mixture was kept at room temperature overnight and the solvent removed under vacuum. The crude product was chromatographed on a silica gel column using a gradient of cyclohexane-$CH_2Cl_2$(1:1–0:11) as eluant to yield the desired compound 3 (1.94 g, 78%): mp 126°–128° C.; $^1$H NMR ($CDCl_3$) δ0.21 (s, 9H, $Si(CH_3)_3$), 4.57 (M, 1H, 4'-H), 4.83 (2 dd, 2H, 5'-H, 5"-H), 5.35 (apparent dd, 1H, 2'-H, $J_{H2',F}$=52.1 Ha), 5.63 (apparent dd, 1H, 3'-H, $J_{H3',F}$=18.4 Hz), 6.30 (dd, 1H, 1'-H, $J_{H1',F}$=20.8 Hz), 7.27–8.13 (m, 16H, aromatic protons, 6-H). Anal. ($C_{35}FH_{31}N_2O_8Si$) C, H, N.

EXAMPLE 2

Synthesis of 5-carboranyl-1-(β-D-ribofuranosyl)uracil (11a) and 5-carboranyl-1-(β-D-xylofuranosyl)uracil (12a).

As illustrated in Scheme 2, 5-iodouracil was converted to 2,4-dichloro-5-iodopyrimidine with phosphorus oxychloride, which on treatment with sodium methoxide yielded 2,4-dimethoxy-5-iodopyrimidine (2a). The latter was coupled with trimethylsilylacetylene in the presence of $(Ph_3P)_2PdCl_2$/CuI, $Et_3N$ in $CH_2Cl_2$ to give 3a, followed by deprotection of the trimethylsilyl group with n-$Bu_4NF$ to give 2,4-dimethoxy-5-ethynylpyrimidine (4a). The coupling of decaborane with the alkyne was first conducted at 110° C. in toluene in the presence of propriononitrile as an activating agent for the decaborane, which is known to give very good yields (>70%) with a variety of terminal alkynes. Unfortunately, when these conditions were applied to the compound 4a, the formation of two products in equal proportion was observed by TLC. The less polar component corresponded to a product which had the two methoxy groups, but no signal for the B-C-H proton by $^1$H NMR, whereas the second more polar product corresponded to the desired compound 5a. A kinetics study of this reaction monitored by TLC showed the initial exclusive formation of the desired product. However, when the reaction was maintained at 110° C., the formation of the less polar product occurred and increased if the reaction was maintained at the same temperature. These observations were confirmed by $^1$H-NMR after quenching the reaction with MeOH at different times. The temperature at which the reaction was performed appeared critical since it had been reported by Heying, T. L. et al. , "A new series of organoboranes. (I) Carboranes from the reaction of decaborane with acetylenic compounds," *Inorg. Chem.* 1963, 2, 1089–1092, that formation of the decaborane-propriononitrile complex occurs only at high temperature. Surprisingly, when the coupling reaction was conducted in the absence of propriononitrile, the formation of the only desired compound 5a was obtained in 60% yield. Demethylation of the methoxy groups using iodotrimethylsilane gave after crystallization in MeOH the desired pure 5-carboranyluracil (6a) exclusively in the closo-form. The absence of the nido-compound [(nido-7,8-$C_2B_9H_{11}$)$^-$] was confirmed by mass spectroscopy and a stain test (spraying the TLC plate with 0.1% $PdCl_2$ in concentrated HCl and heating, produces a gray color for the closo-form and a black color for the nido-form of carboranes) as a white crystalline solid. The availability of 5-carboranyluracil (6a) provided a versatile intermediate for the synthesis of a number of nucleoside analogues described below.

The next step consisted of coupling of silylated 6a with various protected sugars under different conditions. Coupling of silylated 5-carboranyluracil with 1-O-acetyl-2,3,5-tri-O-benzoylribofuranose (7a) and 1,2,3,5-tetra-O-acetyl-xylofuranose (8a), using the Vorbrüggen and Hofle approach (Vorbruggen, H. and Hofle, G, "On the mechanism of nucleoside synthesis," *Chem. Ber.* 1981, 114, 1256–1268) was conducted in the presence of $SnCl_4$ (Scheme 3). The mechanism of the reaction involves the formation of an oxonium ion at the α-face of the sugar moiety (Vorbruggen, supra) which allows the attack of the silylated base on the β-face to give the protected nucleosides 9a and 10a in excellent yield. Deprotection was performed with NaOMe at 4° C., to avoid the formation of the nido-cluster from the closo derivatives, yielded 5-carboranyl-1-(β-D-ribofuranosyl)uracil (11a) and 5-carboranyl-1-(β-D-xylofuranosyl)uracil (12a).

Scheme 2

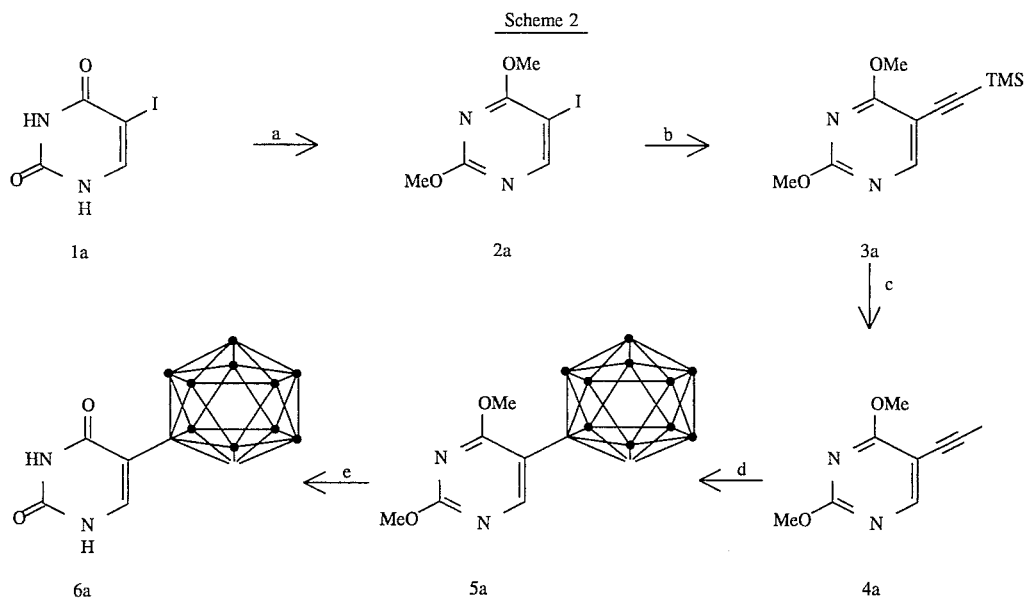

a. POCl$_3$, NaOMe/MeOH; b. HC≡C—TMS, (Ph$_3$P)$_2$PdCl$_2$/CuI, Et$_3$N;

c. n-Bu$_4$NF/THF; d. B$_{10}$H$_{14}$, Toluene; e. TMSI/CH$_2$Cl$_2$.

●: BH, :CH

EXAMPLE 3

Preparation of 3'-thianucleoside by coupling the silylated base 14a with the 1-O-acetyl-2,3-dideoxy-3-thiaribofuranose (13a)

It was desired to prepare a boronated 3'-thianucleoside by coupling the silylated base 14a with the 1-O-acetyl-2,3-dideoxy-3-thiaribofuranose (13a). The oxathiolane, prepared in 5 steps starting from 1,2-butanediol and thioglycolic acid to give the acetate derivative 13a, was coupled to the boronated base 14a using the SnCl$_4$ method developed by Choi, W.-B.; et al., "In situ complexation directs the stereochemistry of N-glycosylation in the synthesis of oxathiolanyl and dioxolanyl nucleoside analogues, "*J. Am. Chem. Soc.*, 113:9377–9379 (1991), yielding a 31:1 ratio of the β-anomer 15a in 82% yield (Scheme 4). After deprotection of the ester, the 5-carboranyl-2',3'-dideoxy-3'-thiauridine (16a) was obtained in 85% yield. This compound had identical chemical characteristics to the compound synthesized from racemic 2',3'-dideoxy-5-iodo-3'-thiauridine, as described by Schinazi, R. F., et al., "*Synthesis of carboranyl-pyrimidine nucleosides: Evidence for intracellular phosphorylation*. Fifth International Symposium on neutron capture therapy, Columbus, Ohio, Sep.13–17, 1992; and Schinazi, R. F., et al., "*Advances in neutron capture therapy*," Soloway, A. H.; Barth, R. F.; Carpenter, D. E., Eds.; Plenum Press: New York and London, pp 285–288 (1993). X-ray crystallography of the nucleoside analogue 16a showed that the base adopted an anti-conformation and the oxathiolane ring was in S3'-exo envelope conformation with a S3'-exo/C2'-endo conformation.

Of significance was the finding that the carboranyl nucleoside had only one conformation. In contrast, the related 5-fluoro nucleoside had a nearly perfect S3'-exo envelope and two different molecules were observed in the asymmetric unit (S3'-exo/C4'-endo and S3'-exo/C2'-endo) (Van Roey, P., et al., "Absolute configuration of the antiviral agent (-)-cis-5-fluoro-1-[2-hydroxymethyl)-1,3-oxathiolan-5-yl]cytosine," *Antiviral Chem. Chemotherapy.* 4:369–375 (1993)). These studies provide conclusive evidence for the closo-configuration for the carboranyl moiety using this chemical approach, and demonstrate the similar planar size of the carboranyl moiety and the pyrimidine base.

Scheme 3

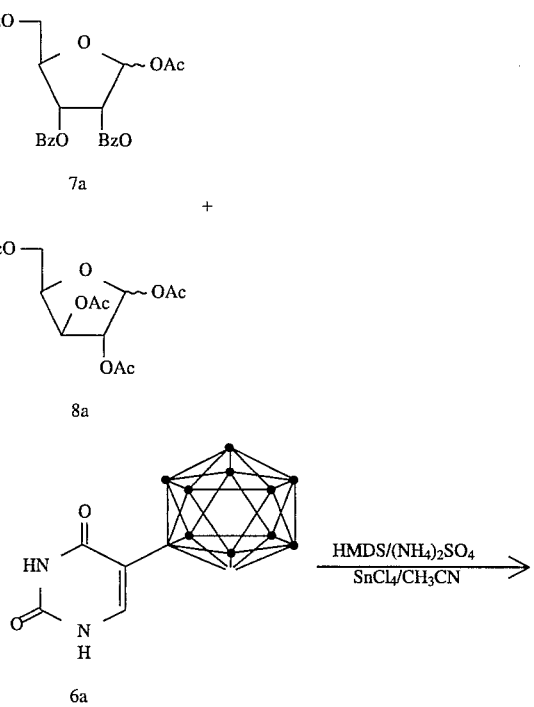

27
-continued
Scheme 3

28
-continued
Scheme 4

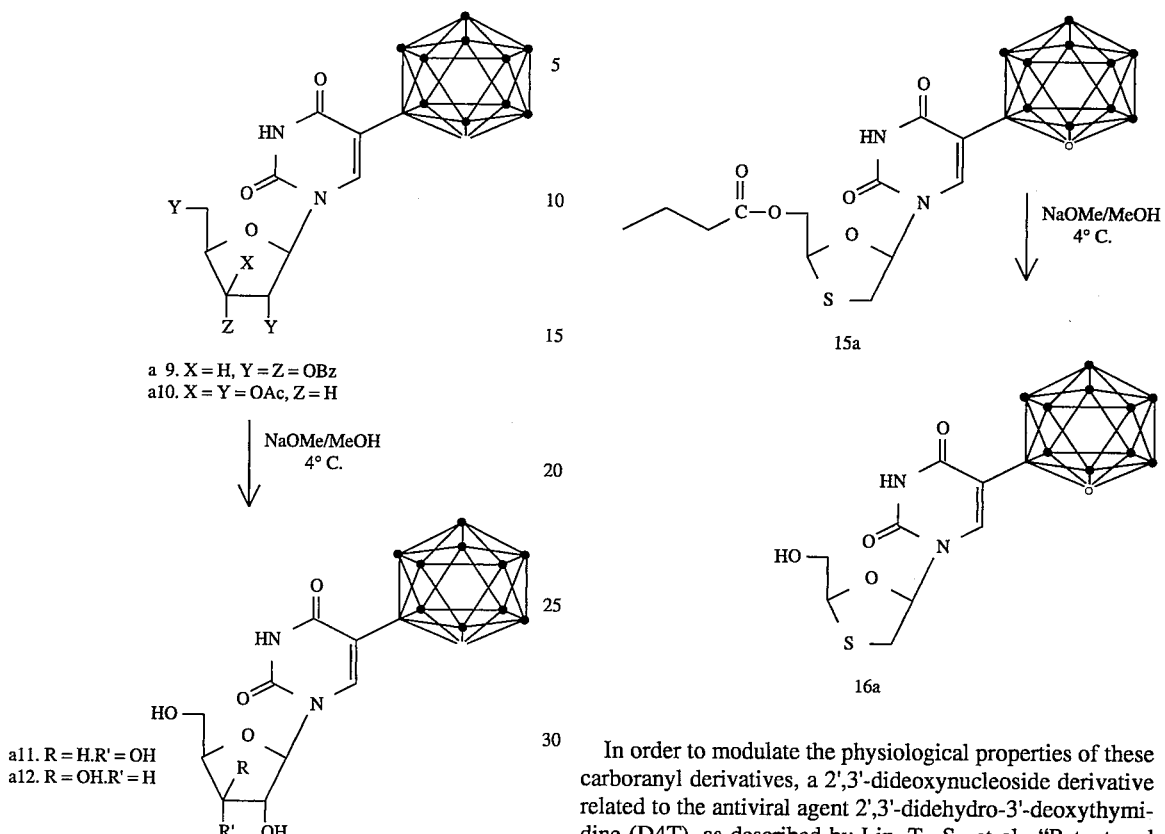

a 9. X = H, Y = Z = OBz
a10. X = Y = OAc, Z = H a11. R = H,R' = OH
a12. R = OH,R' = H

Scheme 4

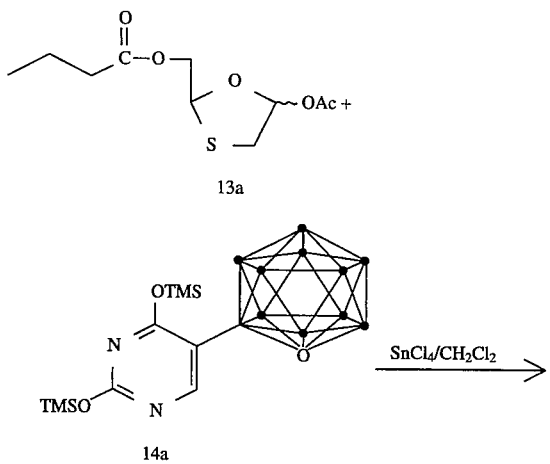

13a

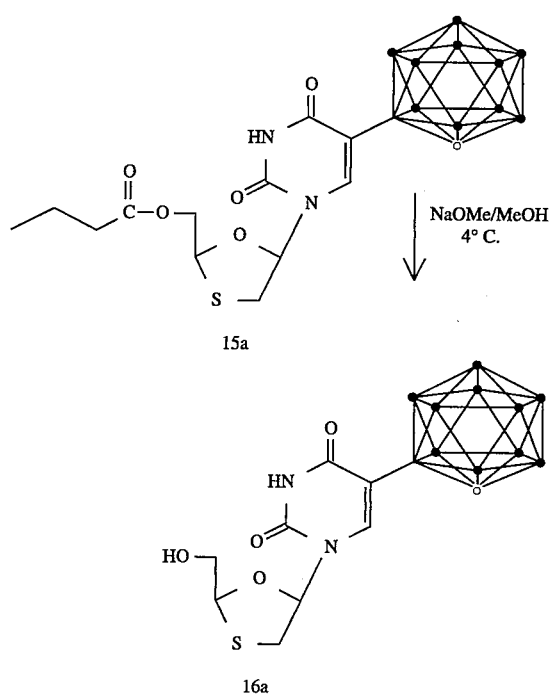

14a

In order to modulate the physiological properties of these carboranyl derivatives, a 2',3'-dideoxynucleoside derivative related to the antiviral agent 2',3'-didehydro-3'-deoxythymidine (D4T), as described by Lin, T. -S., et al., "Potent and selective in vitro activity of 3'-deoxythymidin-2'-ene (3'-deoxy-2',3'-didehydrothymidine) against human immunodeficiency virus," *Biochem. Pharmacol.*, 36:2713–2718 (1987), was synthesized. The strategy developed by Wilson and Liotta to control the stereoselectivity of the N-glycosylation reaction was applied. "A general method for controlling glycosylation stereochemistry in the synthesis of 2'-deoxyribose nucleosides," *Tetrahedron Lett.*, 31:1815–1818 (1990). The 5-(S)-acetoxy-2-(S)-(t-butyldiphenylsilyloxymethyl)-4-(R)-(2,4,6-triisopropyl)phenylthiotetrahydrofuran was prepared starting from the D-glutamic acid in 4 steps. Coupling the protected lactol 17a with the silylated base 14a produced the desired protected compound 18a with a good selectivity in a 76% yield [a 20:1 β:α ratio was obtained, as determined by $^1$H NMR] (Scheme 5). Oxidation of the sulfur group produced compound 19a, but unfortunately basic treatment of the later did not lead to the desired sulfoxide elimination product, but gave a product corresponding to the starting material 6a as well as other uncharacterized compounds. Nevertheless, the coupling of 6a to 17a and related modified sugars demonstrate the versatility of this route towards nucleosides analogues.

Scheme 5

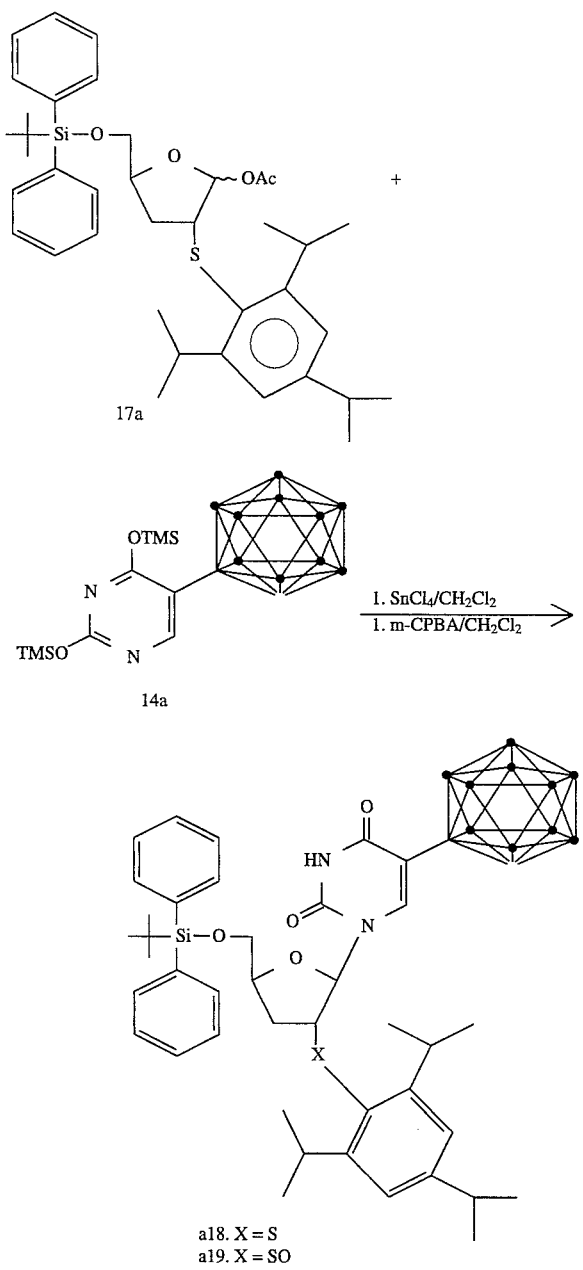

a18. X = S
a19. X = SO

Experimental Section

Melting points were determined on an Electrothermal IA 8100 digital melting point apparatus and are uncorrected. $^1$H and $^{13}$C NMR spectra were recorded on a General Electric QE-300 (300 MHz) spectrometer. UV spectrum were recorded on Shimadzu UV-2101PC spectrophotometer and FTIR spectra were measured on a Nicolet Impact 400 spectrometer. Mass spectroscopy was performed with JEOL [JMS-SX102/SX102A/E] spectrometer. Experiments were monitored using TLC analysis performed on Kodak chromatogram sheets precoated with silica gel and a fluorescent indicator. Column chromatography, employing silica gel (60–200 mesh; Fisher Scientific, Fair Lawn, N.J.), was used for the purification of products. Tetrahydrofuran (THF) was freshly dried and distilled in the presence of sodium benzophenone. Trimethylsilyl iodide and other chemicals, including the carbohydrates, were purchased from Aldrich Chemical Company (Milwaukee, Wis.). Microanalyses were performed at Atlantic Microlab, Inc. (Norcross, Ga.).

5-(Trimethylsilyl)ethynyluracil. The title compound was prepared as described above. m.p. 187°–189° C. (lit. m.p.[23] 189° C.); $^1$H NMR (CDCl$_3$) d 0.23 (s, 9H, 3 CH$_3$), 7.9 (s, 1H, 6-H), 11.55 (m, 2H, 2 NH).

5-Ethynyluracil. This compound was prepared according to the methodology described by Spector, T., et al., "Uracil reductase inactivators for reduction of toxicity of the anti-HIV nucleoside analogue zidovudine," U.S. PCT Int. Appl. WO 92 01, 452 06, Feb. 1992. The physical data are in agreement with the structure of the compound. m.p. 168°–170° C. (lit. m.p. 167° C.); $^1$H NMR (DMSO-d$_6$) d 3.3 (s, 1H, acetylenic proton), 7.5 (s, 1H, 6-H), 11.6 (m, 2H, 2 NH).

2,4-Di-O-acetyl-5-ethynylpyrimidine. A suspension of 5-ethynyluracil (0.5 g, 3.65 mmol) in anhydrous pyridine (30 ml) containing acetic anhydride (18.25 mmol, 1.8 ml) was stirred at room temperature for 18 hours. The resulting clear solution was evaporated to dryness, dissolved in CH$_2$Cl$_2$ and then poured into saturated aqueous NaHCO$_3$. The organic fraction was separated, washed with H$_2$O, dried over MgSO$_4$, filtered and evaporated to dryness under reduced pressure several times with toluene. The crude product was purified by silica gel column chromatography using CH$_2$Cl$_2$/MeOH (9:1) as eluent to yield the title compound (0.63 g, 78%). m.p. 212°–215° C.; $^1$H NMR (CDCl$_3$) d 1.8 (2s, 3H each, 2 CH$_3$), 3.26 (s, 1H, acetylenic proton), 8.25 (s, 1H, 6-H).

2,4-Di-O-benzoyl-5-ethynylpyrimidine. A suspension of 5-ethynyluracil (0.5 g, 3.65 mmol) in anhydrous pyridine (30 ml) containing benzoic anhydride (18.25 mmol, 3.35 ml) was stirred at room temperature for 18 hours. The solution was worked up as described above for the di-O-acyl derivative. (1.02 g, 81%). m.p. 235°–238° C.; $^1$H NMR (CDCl$_3$) d 3.29 (s, 1H, acetylenic proton), 7.45–6.9 (m, 10H, aromatic proton), 8.2 (s, 1H, 6-H).

2,4-Di-O-benzyl-5-ethynylpyrimidine. A suspension of 5-ethynyluracil (0.5 g, 3.65 mmol) in anhydrous THF (30 ml) containing benzyl chloride (18.3 mmol, 2 ml) and sodium hydride (20 mmol; 480 mg) was stirred at room temperature for 18 hours. The excess hydride was destroyed by the slow addition of MeOH. The resulting mixture was treated as described above to yield the desired compound. (0.82 g, 75%). m.p. 212°–216° C.; $^1$H NMR (CDCl$_3$) d 3.25 (s, 2H, CH$_2$—Ph), 3.3 (m, 3H, acetylenic proton and CH$_2$—Ph), 7.4–7.0 (m, 10H, aromatic proton), 8.3 (s, 1H, 6-H).

2,4-Di(trimethylsilyl)-5-ethynylpyrimidine. A suspension of 5-ethynyluracil (0.5 g, 3.65 mmol) in anhydrous 1,1,1,3,3,3-hexamethyldisilazane (50 ml) was stirred at 120° C. for 5 hours. The resulting clear solution was distilled under vacuum and kept under argon and used without purification for the next reaction.

2,4-Dimethoxy-5-iodopyrimidine (2a). The title compound was prepared as previously described by Prystas, M. and Sorm, F., "Nucleic acid components and their analogues, XLIII. Synthesis of anomeric 5-iodo-2'-deoxyuridines," Collec. Czech. Chem. Commun. 29:121–129 (1964). m.p. 65°–67° C. (lit. m.p. 69° C.); $^1$H NMR (CDCl$_3$) d 4.06 and 3.98 (2 s, 6H, 2 OCH$_3$), 8.42 (s, 1H, 6-H); $^{13}$C NMR (CDCl$_3$) d 168.77 (C-4), 165.44(C-2), 164.44 (C-6), 68.91(C-5), 55.04 (OCH$_3$), 55.14 (OCH$_3$).

2,4-Dimethoxy-5-(trimethylsilyl)-ethynylpyrimidine (3a). The title compound was prepared according to the method of Coe and Walker, "The synthesis of 5-substituted-2,4-dimethoxypyrimidines and some related nucleosides analogues," *Nucleosides and Nucleotides*, 11:553–555 (1992). m.p. 72°–74° C. (lit. m.p.[14 a,b] 76° C.); $^1$H NMR (CDCl$_3$) d 0.22 (s, 9H, SiMe$_3$), 3.96 and 4.05 (2 s, 6H, 2 OCH$_3$), 8.36 (s, 1H, 6-H); $^{13}$C NMR (DMSO) d 172.24 (C-4), 165.48 (C-2), 162.83 (C-6), 101.59 (C-5), 101.00 (C acetylenic), 97.09 (C acetylenic), 55.69 (OCH$_3$), 55.14 (OCH$_3$), 0.09 (Si—CH$_3$).

2,4-Dimethoxy-5-ethynylpyrimidine (4a). This compound was synthesized according to the method of Coe and Walker, supra. m.p. 75°–77° C. (lit. m.p. 74° C.; lit. m.p. 83°–84° C.) ; $^1$H NMR (CDCl$_3$) d 3.35 (s, 1H, acetylenic proton), 3.98 and 4.08 (2 s, 6H, 2 OCH$_3$), 8.38 (s, 1H, 6-H); $^{13}$C NMR (CDCl$_3$) d 170.77 (C-4), 164.15 (C-2), 162.02 (C-6), 98.71 (C-5), 83.39 (C-acetylenic), 75.16 (C acetylenic), 54.94 (OCH$_3$), 54.38 (OCH$_3$).

5-Carboranyl-2,4-dimethoxypyrimidine (5a). To a refluxing solution of decaborane (2.52 g, 20.63 mmol) in toluene (70 ml) was added dropwise 2,4-dimethoxy-5-ethynylpyrimidine (3.55 g, 21.62 mmol) in toluene (350 ml). After the addition was completed, the resulted solution was heated under reflux for 30 minutes. The reaction product was cooled and concentrated to dryness in vacuo, and the residue purified by silica gel column chromatography using hexane/ EtOAc (9:1) as eluent to yield 5-carboranyl-2,4-dimethoxypyrimidine (3.435 g; 59%) as a white solid. m.p. 140°–143° C.; $^1$H NMR (CDCl$_3$) d 1.2–3.0 (br, 10H, carborane protons), 4.05 and 4.15 (2 s, 6H, 2 OCH$_3$), 5.38 (s, 1H, carborane proton), 8.56 (s, 1H, 6-H); FTIR (neat, cm$^{-1}$) 2602, 2560, 1594, 1558, 1474, 1404, 1229; MS [FAB (Fast atom bombardment)] m/z 284 (NBA+Li)$^+$ 5-Carboranyluracil (6a). To a solution of 5-carboranyl-2, 4-dimethoxypyrimidine 5a (285 mg, 1 mmol) in CH$_2$Cl$_2$ (10 ml), trimethylsilyl iodide (520 mg, 2.6 mmol) was added under anhydrous conditions at room temperature. The resulting yellow solution was stirred for three hours. The excess of trimethylsilyl iodide and the intermediate trimethylsilyl ethers formed during the reaction were hydrolyzed by addition of MeOH (5 ml). The solution was concentrated to dryness in vacuo, dissolved in CH$_2$Cl$_2$, filtered, and then redissolved in MeOH to give on crystallization the desired product as a white solid, (180 mg, 71%). m.p.>280° C. (dec); $^1$H NMR (DMSO-d$_6$) d 1.2–3.0 (br, 10H, carborane protons), 5.90 (s, 1H, carborane proton), 7.64 (s, 1H, 6-H), 11.28 (br s, 2H, NH, D$_2$O exchangeable). $^{13}$C NMR (CDCl$_3$) d 162.82 (C-4), 150.49 (C-2), 144.84 (C-6), 105.84 (C-5), 72.40 (C—C-5), 59.61(C—H). FTIR (KBr, cm$^{-1}$) 3222, 3082, 2839, 2572, 1715, 1685, 1448; UV (MeOH) 1$_{max}$=268 nm (e=9500), 1$_{max}$=216 nm (e=10020), 1$_{min}$=236 nm (e=2500); MS [EI (Electronic impact)], m/e 254 (M)$^+$.

5-Carboranyluridine (11a). To a suspension of 5-carboranyluracil 6a (127 mg, 0.5 mmol) in dry CH$_3$CN (10 ml) was added sequentially 1-O-acetyl-2,3,5-tri-O-benzoyl-b-D-ribofuranose (265 mg, 0.525 mmol), hexamethyldisilazane (HMDS, 85 ml), and chlorotrimethylsilane (TMSCl, 51 mL) and the mixture was stirred under a N$_2$ atmosphere at room temperature. After 5 minutes, SnCl$_4$ (71 ml, 0.6 mmol) was added and the mixture was stirred for 1.5 hours and then saturated NaHCO3 was added while stirring. The resulting suspension was filtered through Celite, and washed with warm CHCl$_3$. The combined organic fractions were dried over Na$_2$SO$_4$ and concentrated to dryness under vacuum. The residue was dissolved in dry MeOH, NaOMe (100 mg) was added, and the reaction mixture was stirred for 6 hours at 4° C. Dowex H$^+$ resin was added and the reaction mixture was filtered, evaporated to dryness, then chromatographed using CH$_2$Cl$_2$/MeOH, (90/10) as eluent to give pure 5-carboranyluridine (182 mg, 72%). m.p. 277°–279° C. (lit. m.p. 279°–280° C.). This material had identical characteristics to a sample generously provided by Y. Yamamoto (Department of Chemistry, Faculty of Science, Tohoku University, Sendai 980, Japan).

5-Carboranyl-xylofuranosyluracil (12a). A suspension of 5-carboranyluracil (6a) (127 mg, 0.5 mmol) in dry CH$_3$CN (10 mL) was added sequentially tetra-O-acetyl-b-D-xylofuranose (265 mg, 0.525 mmol), HMDS (85 ml), and TMSCl (51 mL) while stirring under a N$_2$ atmosphere at room temperature. The mixture was treated as described for compound 11a to yield pure 5-carboranylxylofuranosyluracil (172 mg, 68 %). m.p. 274°–278° C.; $^1$H NMR (CDCl$_3$) d 1.3–2.8 (bm, 10H, —BH), 2.9 (m, 1H, 2'-H), 3.4–4.1 (m, 4H, 3'H, 3"-H, 5'-H and 5"-H), 4.6 (m, 1H, 4'-H), 4.8 (m, 2H, 2'-OH and 3'-OH), 5.25 (t, 1H, 5'-OH), 5.68 (d, 1H, 1'-H; J$_{1',2}$=6.02 Hz), 5.77 (bs, 1H, —B—CH), 7.98 (s, 1H, 6-H), 8.82 (s, 1H, NH); MS [LSIMS (Liquid secondary ion mass spectroscopy)] m/z 387 (M+H)$^+$.

5-Carboranyl-2',3'-dideoxy-3'-thiauridine (16a). To the silylated 5-carboranyluracil 14a (0.2 g, 0.78 mmol) in dry CH$_2$Cl$_2$ (20 ml), a SnCl$_4$ solution (1.05 mmol, 1.05 ml, 1M solution in CH$_2$Cl$_2$) was added under a N$_2$ atmosphere. The mixture was stirred for 30 minutes at room temperature and then added to the acetate 13a (0.23 g, 0.94 mmol) in CH$_2$Cl$_2$ (20 ml). After 2 hours, the reaction was quenched with a mixture of NH$_4$OH/CH$_2$Cl$_2$ (1:20, 50 ml) resulting in the formation of a white precipitate (tin salt). The mixture was allowed to stir for another 30 minutes, and then it was partially purified using a short silica gel column which was eluted sequentially with CH$_2$Cl$_2$, EtOAc, and EtOAc:EtOH (9:1; 100 mL). The filtrates were combined and evaporated under reduced pressure and dissolved in dry MeOH. To this solution, NaOMe (150 mg) was added and the mixture was maintained at 4° C. for 6 hours. Water (5 ml) was then added and the solution was neutralized using Dowex H$^+$ resin and then filtered. The filtrates were evaporated and the residual solid was then column chromatographed on silica gel using CH$_2$Cl$_2$/MeOH (9:1) as eluent to give the title compound (238 mg, 82%). m.p. 256°–259° C. (lit. m.p. 259° C.).

1-[5'-(S)-Acetoxy-2'-(S)-(t-butyldiphenylsilyloxymethyl)-4'-(R)-(2,4,6-triisopropyl)phenylthiotetrahydrofuran] -5-carboranyluracil (18a). To silylated 5-carboranyluracil 14a (0.2 g, 0.78 mmol) in dry CH$_2$Cl$_2$ (20 ml), a SnCl$_4$ solution (1.05 mmol, 1.05 ml, 1M solution in CH$_2$Cl$_2$) was added under N$_2$ atmosphere. The mixture was stirred for 30 minutes at room temperature and then added to the acetate 17a (0.93 mmol, 0.54 g) dissolved in CH$_2$Cl$_2$ (10 ml) at 0° C. The reaction was worked up as described for compound 16a to give the title compound as a light yellow solid (0.56 g, 76%). $^1$H NMR (CDCl$_3$) d 0.8–1.2 (m, 30 H, 3CH(CH$_3$) and C(CH$_3$)$_3$), 1.3–2.8 (bm, 10H, —BH), 2.9 (m, 1H, 2'-H), 3.4–4.1 (m, 4H, 3'-H, 3"-H, 5'-H and 5"-H), 4.6 (m, 1H, 4'-H), 5.78 (d, 1H, 1'-H; J$_{1',2}$=6.22 Hz), 5.67 (bs, 1H, —B—CH), 7.0–7.7 (m, 12 H, 2 Ph and 2 aromatic proton), 7.98 (s, 1H, 6-H), 8.82 (s, 1H, NH).; HRMS (High resolution mass spectroscopy) calcd. for B$_{10}$C$_{42}$H$_{62}$N$_2$O$_4$SSi m/z 829.1234, found 829.1253.

1-[5'-(S)-Acetoxy-2'-(S)-(t-butyldiphenylsilyloxymethyl)-4'-(R)-(2,4,6-triisopropyl)phenylsulfoxide-tetrahydrofuran]-5-carboranyluracil (19a). Compound 18a (0.1 g, 3.13 mmol) was dissolved in dry CH$_2$Cl$_2$ (30 ml). To this solution, a solution of m-chloroperbenzoic acid (0.69 g, 3.4 mmol) in dry CH$_2$Cl$_2$ (30 ml) was added dropwise at 0° C., and the mixture was stirred at 0° C. for 2 hours. The mixture was poured into a saturated aqueous solution of NaHCO$_3$ and extracted with CH$_2$Cl$_2$ three times. The organic layer was dried over anhydrous MgSO$_4$, and then evaporated under reduced pressure to give a yellow oil (60 mg, 72%). $^1$H NMR (CDCl$_3$) d 0.8–1.2 [m, 30 H, 3CH(CH$_3$) and C(CH$_3$)$_3$], 1.3–2.8 (bm, 10H, —BH), 3 (m, 1H, 2'-H), 3.6–4.1 (m, 4H, 3'-H, 3"-H, 5'-H and 5"-H), 4.8 (m, 1H, 4'-H), 5.84 (d, 1H, 1'-H; J$_{1',2'}$=6.22 Hz), 5.72 (bs, 1H, —B—CH), 7.2–7.8 (m, 12 H, 2 Ph and 2 aromatic proton), 8.02 (s, 1H, 6-H), 8.9 (s, 1H, NH). HRMS calcd for B$_{10}$C$_{42}$H$_{62}$N$_2$O$_4$SSi m/z 845.1228, found 845.1254.

B. Preparation of nucleosides containing a 3'-O-[(o-carboran-1-yl-ethyl)phosphonate] moiety and dinucleotides that contain a 3',5'-O,O-[(o-carboran-1-yl-methyl)phosphonate] linkage A novel method is provided for the preparation of nucleosides containing a 3'-O-[(o-carboran-1-yl-methyl)phosphonate] moiety and dinucleotides that contain a 3',5'-O,O-[(o-carboran-1-yl-methyl)phosphonate] linkage. The method involves the use of the key starting material, O-methyl(o-carboran-1-yl)methyl phosphonate, a new and versatile borophosphonylating agent.

Figure 4:
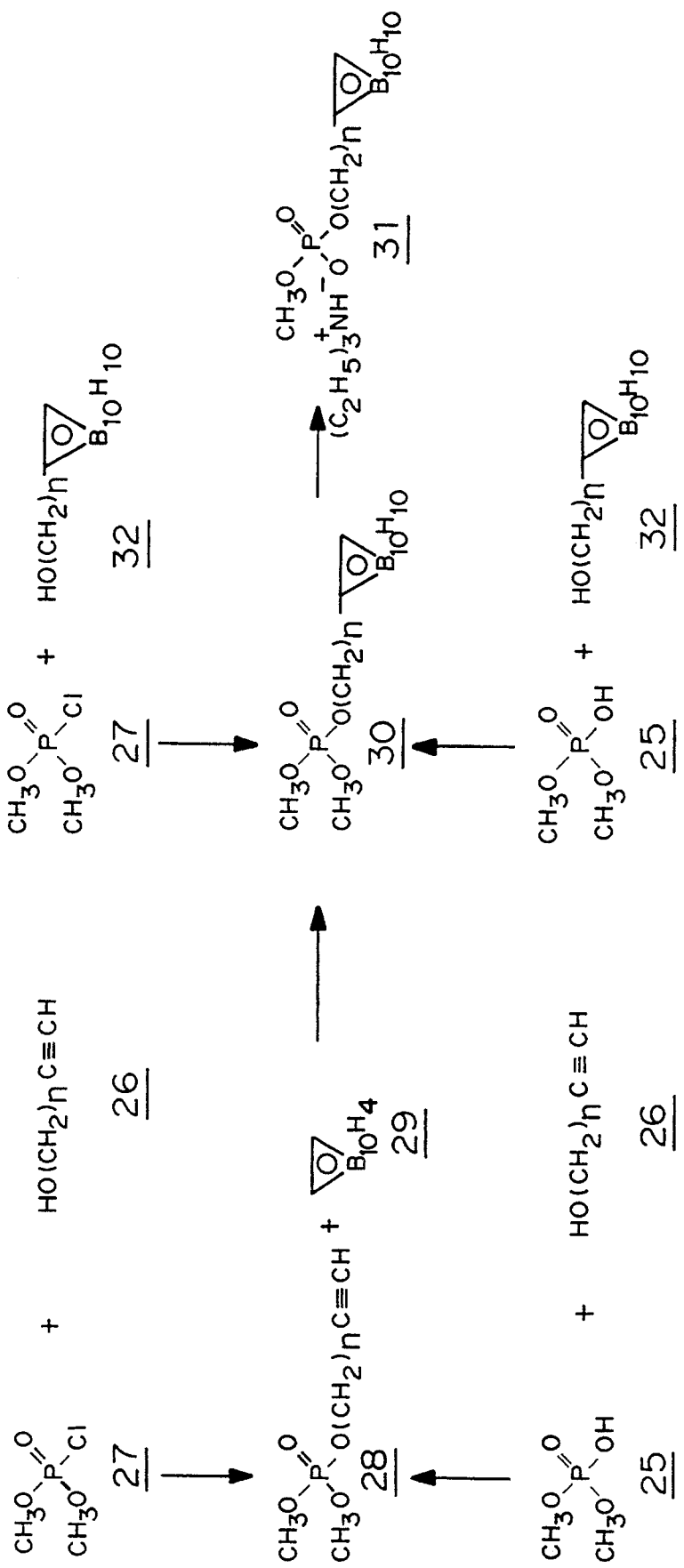
FIG. 4 is an illustration of a process for the preparation of O-methyl-[O-(o-carboran-1-yl)alkyl]phosphate.

As illustrated in FIG. 4, O-methyl(o-carboran-1-yl)methyl phosphonate can be prepared in a three step procedure. In the first step, propargyl bromide is reacted with trimethyl phosphite in a Michaelis-Arbuzov type reaction to yield O,O-dimethylpropargylphosphonate in good yield. Propargyl bromide can be obtained from Aldrich Chemical Company as a solution in toluene, and toluene is used as the reaction solvent. A range of other solvents can also be used in this step (see, for example, Arbuzov, B. A., *Pure Appl. Chem.*, 9:307–335 (1964)). The reaction can be carried out at any temperature, and for any time period that achieves the desired results. The reaction is usually carried out at a temperature ranging from −20° C. to the boiling temperature of the solvent. It is preferable to limit the access of moisture and oxygen. The reaction time depends upon the structure of the substrate used, the solvent, and the temperature of reaction, and is typically from 1 to 24 hours.

Alkynyl starting materials other that propargyl bromide can be used in this process. Propargyl iodide or propargyl chloride can be substituted for propargyl bromide. As can be surmised by one of ordinary skill in the art given this disclosure, 3-butyn-1-bromide will provide a carboranylethylphosphonate, and 4-pentyn-1-bromide will give carboranylpropylphosphonate. In general, appropriately selected homologs of propargyl bromide can be used to prepare any carboranyl (CH$_2$)$_n$P isomer of interest.

In the second step, O,O-dimethylpropargylphosphonate is reacted with decaborane in acetonitrile, according to the general reaction scheme described by Heying, et al., *Inorg. Chem.*, 1089–1092 (1963), to provide O,O-dimethyl(o-carboran-1-yl)methylphosphonate in good yield. The reaction is typically carried out in a Lewis base solvent, such as acetonitrile, propionitrile, amine, dialkyl sulfide, cyclic or acyclic ether (tetrahydrofuran, dioxane, diethyl and diisopropyl ether), or an aromatic solvent as benzene. The reaction can be carried out at any temperature and for any time period that achieves the desired results. The temperature of reaction generally ranges from room temperature to the boiling temperature of solvent, and the time period of reaction, which depends on the structure of the substrate and reaction conditions, is, in general, from 1 to 24 hours.

The target key starting material O-methyl(o-carboran-1-yl)methyl phosphonate is obtained as a triethylamine salt on demethylation of O,O-dimethyl(o-carboran-1-yl)methylphosphonate using thiophenol and triethylamine in dioxane. A mixture of thiophenol or thiocresol and triethylamine, diisopropylamine or 1,8-diazabicyclo[5.4]undec-7-ene (DBU base) or other organic base in dioxane or other chemically inert solvent can alternatively be used. In another embodiment, 2-mercaptobenzothiazole is used in combination with diisopropylamine (see *Tetrahedron Lett.*, 29:5479–5482 (1988)). In general, a base should be used that forms a salt of O-methyl(o-carboran-1-yl)methyl phosphonate that is soluble in the organic solvent used. While organic bases are preferred, some inorganic counterions may be used, such as cesium (obtained from cesium hydroxide).

This method is used in oligonucleotide chemistry to deblock internucleotide linkages protected with an O-methyl group. In contrast, selective demethylation using t-butylamine is only partially successful, as several uncharacterized by-products are obtained. This may be due to partial closo to nido carboranyl transformations.

The key starting material, O,O-dimethyl(o-carboran-1-yl)methylphosphonate, triethylammonium salt, is reacted with a 5'-(and 2'- or base-, if appropriate) protected nucleoside in the presence of triisopropylbenzenesulfonyl-chloride as the activating agent and 2,4,6-collidine and 1-methylimidazole. Triisipropylbenzenesulfonyl chloride is an activating agent which activates the borophosphonylating agent. 2,4,6-Collidine is a scavenger of the hydrochloric acid generated during reaction. 1-Methylimidazole is a nucleophilic catalyst which additionally activates the borophosphonylating agent. Instead of triisipropylbenzenesulfonyl chloride other arylsulfonyl chlorides, or arylsulfonylazolides can be used. In place of 2,4,6-collidine other organic bases can be used, such as di(isopropyl)ethylamine. 1-Methylimidazole can be replaced by other nucleophilic catalysts such as 5-chloro-1-ethyl-2-methylimidazole and 5-nitro-1-methylimidazole. The reaction is typically run in an inert organic solvent, such as a cyclic ether as tetrahydrofuran, a nitrile such as acetonitrile, or a chlorinated hydrocarbon such as dichloromethane at a temperature ranging from −10° C. to boiling temperature of solvent for a time ranging from 5 minutes to 24 hours under anhydrous conditions.

The product of reaction, a 3'-O-[O-methyl-(o-carboran-1-ylmethyl)phosphonated]nucleoside, is demethylated as described above to provide the triethylamine salt of a 3'-O-[(o-carboran-1-yl-methyl)phosphonated] nucleoside.

In an alternative embodiment, if a 5'-O-[(o-carboran-1-yl-methyl)phosphonate] nucleoside is desired, the above steps can be carried out using a 3'- (and 2'- or base-, if appropriate) protected nucleoside. However, due to the higher chemical activity of the 5'-hydroxyl group, the reaction conditions should be adjusted. Additionally, the solubility of a nucleoside bearing a free 5'-hydroxyl group in general is lower than that with a free 3'-hydroxyl group when the 5'-hydroxyl is protected, and therefore, adjustment of the solvent may be necessary.

The triethylamine salt of the 3'-O-[(o-carboran-1-yl-methyl)phosphonated] nucleoside can then be reacted under anhydrous conditions with a 3'-(2'-and base protected, if appropriate) nucleoside to provide a dinucleotide with a 3',5'-O,O-[(o-carboran-1-yl-methyl)phosphonate] linkage. In an alternative embodiment, a 5'-ester can be reacted with a 3'-hydroxyl group of a second nucleoside.

FIG. 3 is a schematic illustration of a process for the preparation of thymidine-(3',5')-thymidine (o-carboran-1-yl)methylphosphonate using the key starting material O-methyl(o-carboran-1-yl)methyl phosphonate. The process is described in detail in Example 4. Column chromatography was performed on silica gel 60, 230–400 mesh from Aldrich (Milwaukee, Wis.). Thin layer chromatography was performed on silica gel F 254 plates from Sigma (St. Louis, Mo.). Solvents were purchased in the highest available quality and used without drying. Mass spectra were recorded on a VG 70-S or Perkin-Elmer Sciex API-3 spectrometer. $^{31}$P NMR spectra were recorded on a Bruker WP-200 spectrometer operating at 81.0 MHz with 85% $H_3PO_4$ used as an external standard. $^1$H and $^{13}$C NMR spectra were recorded on a GE QE Plus spectrometer operating at 300.15 MHz and 75.48 MHz, respectively, with tetramethylsilane as the external standard. Shifts downfield from the standard were assigned as positive. UV spectra were recorded on a Beckman DU-65 spectrophotometer. Reversed phase high performance liquid chromatography (RP-HPLC) was performed on a Hewlett-Packard 1050 system using a Whatman Partisphere C18 5 μm, 4.7×235 mm column.

EXAMPLE 4

Preparation of thymidine-(3',5')-thymidine (o-carboran-1-yl)methylphosphonate

O,O-Dimethylpropargylphosphonate (3). Propargyl bromide (2, FIG. 3) [0.15 mol, 22.3 g of 80% solution in toluene], and trimethylphosphite (1) (0.19 mol, 23.6, 25% molar excess) were stirred under reflux for 5 hours, and then distilled. The low boiling fractions consisted mainly of unreacted 2 and O,O-dimethylmethylphosphonate as a main by-product. The fraction boiling at 50°–67° C./0.5 mm Hg was collected and redistilled yielding 3. Bp 69°–91° C./1 mm Hg (9.5 g, 45%). $^{31}$P NMR (CDCl$_3$): δ 21.0, $^1$H NMR (CDCl$_3$): δ 2.8 (dd, 2H, $J_{PH}$=18.4 Hz, $J_{H1H3}$=2.5 Hz, PCH$_2$), 3.8 (d, 1H, $J_{PH}$=9.5 Hz, CH), 3.9 (d, 6H, $J_{PH}$=13.8 Hz, CH$_3$OP), $^{13}$C NMR (CDCl$_3$): δ 16.0 (d, $J_{PC}$=145.8 Hz, PCH$_2$), 53.0 (d, $J_{PC}$=6.8 Hz, CH$_3$OP). 71.2 (d, $J_{PC}$=10.6, CH), 73.4 (d, $J_{PC}$=14.3. CH$_2$C).

O,O-Dimethyl(o-carboran-1-yl)methylphosphonate (5). Method A. Decaborane (4) (0.01 mol, 1.2 g) was dissolved in dry CH$_3$CN (20 mL) and the resulting solution was heated under reflux. After 15 minutes, 3 (0.02 mol, 2.8 g) was added to the boiling solution and heating continued for 8 hours. The reaction mixture was left overnight at room temperature and then filtered. The solvent was evaporated under reduced pressure and the oily residue was redissolved in CH$_2$Cl$_2$ (25 mL). The resulting solution was washed with H$_2$O (3×20 mL) and the organic phase was dried over MgSO$_4$ and evaporated. The oily residue was redissolved in CH$_2$Cl$_2$ (20 mL), and then precipitated with hexanes (250 mL). The precipitate was filtered and hexanes evaporated under reduced pressure to provide an oily residue which crystallized spontaneously. The crystals were washed with hexanes and dried under reduced pressure. For analysis, the resultant product was recrystallized from hexanes (yield 1.1 g, 40%).

Method B. Decaborane (4) (0.02 mol, 2.4 g) was dissolved in dry toluene (350 mL) and then propionitrile (0.34 mol, 18.7 g) was added. The resulting solution was heated under reflux for 15 minutes and then 3 (0.017 mol, 4.5 g) was added. The solution was heated under reflux for five hours, and then the reaction mixture was left overnight at room temperature. Product 5 was isolated as described in Method A; yield 1.6 g, 36%. Fine white flakes, mp 68°–70° C.; anal. calcd. for $C_5H_{19}PO_3B_{10}$: C, 22.55: H, 7.19. Found: C, 22.74; H, 7.21; $^{31}$P NMR (CDCl$_3$) δ 20.7; $^1$H NMR (CDCl$_3$) δ 0.8–3.4 (b signal, 10 H, CCHB$_{10}$H$_{10}$) 2.8 (d, 2H, $J_{PH}$=20.3 Hz, PCH$_2$), 3.7 (d, 6H, $J_{PC}$=10.2 Hz, CH$_3$OP), 4.4 (b s,1H, CH); $^{13}$C NMR (CDCl$_3$, δ 33.2 (d, $J_{PC}$=144.2 Hz, PCH$_2$), 53.0 (d, $J_{PC}$=6.8 Hz, CH$_3$OP), 59.84 and 67.3 (s and s, CCHB$_{10}$H$_{10}$).

O-Methyl(o-carboran-1-yl)methylphosphonate, Et$_3$N salt, (6). Compound 5 (0.66 g, 2.5 mmol) was dissolved in dioxane (5 mL), and thiophenol (10 mL) and triethylamine (10 mL) were added. After two hours at room temperature, the reaction mixture was evaporated and the oily residue dissolved in CH$_2$Cl$_2$ and triturated with hexanes, then centrifuged to remove insoluble impurities. The hexanes were evaporated, yielding 6 as an oil which crystallized on cooling. The yield of crude product 6, which contained traces of thiophenol, was 0.7 g (79%). Crude 6 can be used directly for the synthesis of 8. For analytical purposes, 6 was purified by means of silica gel chromatography using 0–50% CH$_3$OH in CH$_2$Cl$_2$ as eluent. $^{31}$P NMR (CDCl$_3$) δ 14.8: $^1$H NMR (CDCl$_3$); δ 1.3 (t, 9H, $J_{HH}$=7.4 HZ, CH$_3$), 1.0–3.1 (b signal,10H. CCHB$_{10}$H$_{10}$), 2.6 (d, 2H, $J_{PH}$=18.4 Hz, PCH$_2$), 3.0–3.1 (m, 6H, NCH$_2$), 3.6 (d, 6H, $J_{PH}$=9.2 HZ, CH$_3$OP), 4.7 (b s, 1H, CH); $^{13}$C NMR (CDCl$_3$) δ 8.52 (s, CH$_3$CH$_2$N), 34.20 (d, $J_{PC}$=133.0 Hz, PCH$_2$), 45.77 (s, CH$_3$CH$_2$N), 52.00 (d, $J_{PC}$=5.9 Hz, CH$_3$OP), 60.38 and 70.00 (s and s, CCHB$_{10}$H$_{10}$).

5'-O-Monomethoxytritylthymidine 3'-O-[O-methyl(o-carboran-1-yl)methylphosphonate] (8). Compound 6 ( 0.2 g, ca. 0.6 mmol) and triisopropylbenzenesulfonylchloride (0.3 g, 1.0 mmol) were dissolved in dry THF (1.0 mL) and then 2,4,6-collidine (0.13 mL, 1.0 mmol) was added with stirring. After 15 minutes at room temperature, 5'-O-monomethoxytritylthymidine 7 (0.15 g, 0.3 mmol) dissolved in dry THF (0.3 mL) was added, followed by 1-methylimidazole (0.1 mL, 2.0 mmol). After 2 hours at room temperature, the reaction mixture was evaporated to dryness. The residue was dissolved in CH$_2$Cl$_2$ (5 mL). The resultant solution was washed with H$_2$O (3×5 mL). The organic fraction was dried over MgSO$_4$ and evaporated to dryness. The crude product was purified by silica gel column chromatography using a stepwise 0–2% gradient of CH$_3$OH in CH$_2$Cl$_2$ as eluent. Fractions containing 8 were collected, and the organic solvents evaporated to dryness. The residue was dissolved in CH$_2$Cl$_2$ and precipitated from hexanes. The precipitate was dried under vacuum yielding 8 as a mixture of two diastereoisomers (0.1 g, 44%). TLC R$_f$ 0.30 and 0.37 (94:6 CH$_2$Cl$_2$—CH$_3$OH ); UV (95% C$_2$H$_5$OH) λ 265.7 nm, λ$_{min}$, 250.0 nm, λ 230.0 nm: $^{31}$P (CDCl$_3$) δ 33.0: $^1$H NMR (CDCl$_3$) δ 1.2 [s, 3H, CH$_3$(5)], 0.9–3.1 (b signal, 10H, CCHB$_{10}$H$_{10}$), 2.3–2.6 (m and m, 2H, H2'), 2.7 and 2.8 (d and d, 2H, $J_{PH}$=18.4 Hz, PCH$_2$), 3.4 and 4.2 (d and d, 2H, $J_{HH}$=9.0, H5'), 3.6 and 3.7 (d and d, 3H, $J_{PH}$=9.0 Hz, CH$_3$OP), 3.5–3.6 (m, 1H, H4'), 3.8 (s, 3H, CH$_3$OPh), 4.3 and 4.4 (b s and s,1H, CH), 5.1 (b m, 1H, H3'), 6.4 (t, 1H, $J_{HH}$=4.5 Hz, H1'), 7.8–7.9 and 7.2–7.4 (m and m, 14H, arom.), 7.5 and 7.6 (s and s,1H, H6), 8.5 and 8.6 (s and s, 1H, H3); $^{13}$C NMR (CDCl$_3$) δ 11.71 [s, CH$_3$(5)], 35.03 (s, C2'), 39.25 (d, PCH$_2$, $J_{PC}$=34.6), 53.26 (d, CH$_3$OP, $J_{PC}$=5.1Hz), 55.17 (s, CH$_3$OPh), 59.74 (s, C5'), 63.06 (C3'), 62.86 and 66.56 (s and s, CCHB$_{10}$H$_{10}$) , 84.25 and 84.59 (s and s, C1'), 87.46 and 87.53 (s and s, C4'), 113.29 and 113.32 (s and s, C5), 127.40, 128.03, 128.18, 128.23, 130.24, 136.77, 143.34, 158.88 (singlets, arom.), 134.32 and 134.38 (s and s, C6), 150.14 and 150.77 (s and s, C2), 163.28 (s, C4).

5'-O-Monomethoxytritylthymidine-3'-O-(o-carboran-1-yl)methylphosphonate, Et$_3$N salt (9). Compound 8 (40 mg, 0.05 mmol) was dissolved in dioxane (0.1 mL), and thiophenol (0.2 mL) and triethylamine (0.2 mL) were added. After 5 minutes at room temperature, the reaction mixture was precipitated with diethyl ether and centrifuged to remove insoluble impurities. The ether supernatant containing product was evaporated to dryness, and the residue dissolved in CH$_2$Cl$_2$ and precipitated twice with hexanes. The yield of chromatographically homogeneous 9 was 29 mg (70%). TLC $R_f$ 0.08 (9:1 $CH_2Cl_2$—$CH_3OH$), 0.54 (9:1 $CH_3CN$—$H_2O$); UV (95% $C_2H_5OH$) $\lambda_{max}$ 267.0 nm, $\lambda_{min}$ 244.2 nm; $^{31}P$ NMR ($CDCl_3$) δ 12.85; $^1H$ NMR ($CDCl_3$) δ 1.3 (t, 9H, $J_{HH}$=7.3 Hz, $CH_3$), 1.4 [s, 3H, $CH_3$(5)], 0.6–3.2 (b signal, 10H, $CCHB_{10}H_{10}$), 2.5 (d, 2H, $J_{PH}$=18.4 Hz, $PCH_2$, 2.9–3.1 (m, 6H, $NCH_2$), 3.3 and 3.5 (d and d, 2H, $J_{HH}$=9.0, H5'), 3.8 (s, 3H, $CH_3OPh$), 4.1 (b s, 1H, H4'), 4.8 (b t, 1H, H3'), 4.9 (b s, 1H, CH), 6.4 (m, 1H, 1H'), 6.9 and 7.1–7.4 (d and m, 14 H, arom.), 7.6 (s, 1H, H6), 9.3 (s, 1H, H3); $^{13}C$ NMR ($CDCl_3$) δ 8.54 (s, $CH_3CH_2N$), 11.70 [s, $CH_3$(5)], 36.50 (d, $J_{PC}$=102.0 Hz, $PCH_2$, 40.05 (s, C2'), 45.66 (s, $CH3CH_2N$), 55.23 (s, $CH_3OPh$), 60.34 (s, C5'), 76.24 (C3'), 70.05 and 75.65 (s and s, $CCHB_{10}H_{10}$), 84.55 (s, C1'), 87.23 (s, C4'), 113.31 (s, C5), 127.10, 127.31, 127.83, 128.00, 128.35, 128.41, 129.20, 134.00, 135.50, 144.45, 157.25 (singlets. arom.). 130.38 (s, C6), 151.05 (s, C2), 164.05.(s, C4).

5'-O-Monomethoxytritylthymidine(3',5')3'-O-acetylthymidine(o-carboran-1-yl)methylphosphonate (11). Compound 9 (16 mg, 0.02 mmol) and triisopropylbenzenesulfonyl chloride (8 mg, 0.025 mmol) were dissolved in dry $CH_3CN$ (0.2 mL), and 2,4,6-collidine (5 µl, 0.035 mmol) was added with stirring. After 15 minutes at room temperature, a solution of 3'-O-acetylthymidine (10) (10 mg, 0.035 mmol) in dry $CH_3CN$ (0.05 mL) followed by 1-methylimidazole (2 µL, 0.025 mmol) were added to the mixture. The mixture was left overnight at room temperature and then $CH_2Cl_2$ (1 mL) was added. The resultant solution was washed with water (4×0.5 mL), and the organic layer separated, dried over $MgSO_4$, and evaporated to dryness. The crude product was purified by silica-gel column chromatography using a stepwise 0–3% gradient of $CH_3OH$ in $CH_2Cl_2$ as eluent. Fractions containing 11 were collected and the organic solvents evaporated to dryness. The residue was dissolved in dichloromethane and precipitated from hexanes. The resultant precipitate was dried under vacuum yielding 11, yield 6 mg, 30%. TLC $R_f$ 0.56 (9:1 $CH_2Cl_2$—$CH_3OH$), UV (95% $C_2H_5OH$) $\lambda_{max}$ 265.0 $\lambda_{min}$ 245.0 nm, $\lambda_{sh}$ 229.0 nm; MS/LSI(FAB$^+$) 1016 [M+2Li]; $^{31}P$ NMR ($CDCl_3$) δ 21.16 and 22.95; $^1H$ NMR ($CDCl_3$) δ 1.23 [d, 3H, $J_{HH}$6=3 Hz, $CH_3$(5)], 1.44 [s, 3H, $CH_3$(5)], 1.50–1.72 and 2.24–2.48 (b m and b m, 2H and 2H, H2'), 0.6–3.2 (b signal, 10H, $CCHB_{10}H_{10}$), 1.88 (d, $J_{PH}$=8.5 Hz, 2H, $PCH_2$), 2.07 (s, 3H, $CH_3CO$), 3.35–3.58 (m, 2H, H5'), 3.78 (s, 3H, $CH_3OPh$), 3.85–4.4 (mm, 4H, H5' and H4'), 5.0 (b s, 1H, CH), 5.10–5.25 (b m, 1H, H3'), 6.0–6.4 (b mm, 3H, H3', H1'), 6.70–6.85 and 7.10–7.50 (14H. arom.).

Thymidine (3', 5')thymidine(o-carboran-1-yl)methylphosphonate (12). Compound 11 (4.5 mg, 4.5 µmol) was dissolved in $CH_3OH$ (0.15 mL), concentrated $NH_4OH$ (25%, $NH_3$) was added (0.15 mL), and the reaction mixture maintained at room temperature for 30 minutes (TLC monitoring, solvent system 9:1 $CH_2Cl_2$—$CH_3OH$). The solvent was evaporated to dryness yielding 5'-O-monomethoxytrityl-thymidine(3',5')thymidine (o-carboran-1-yl)methylphosphonate as a white solid [TLC $R_f$ 0.44 (9:1 $CH_2Cl_2$—$CH_3OH$)]. Crude 5'-O-monomethoxytritylthymidine(3', 5')thymidine-o-carboran-1-yl)methylphosphonate (≈4.5 µmol) was dissolved in 80% acetic acid (0.5 mL) and heated at 60° C. After approximately 30 minutes (TLC monitoring, 9:1 $CH_2Cl_2$:$CH_3OH$) acetic acid was coevaporated with n-butyl alcohol. The crude product was dissolved in pyridine-$CH_2Cl_2$ and after precipitation with hexanes purified by silica gel column chromatography, using a stepwise 0–10% gradient of $CH_3OH$ in $CH_2Cl_2$ as eluent. Compound 12, isolated as a mixture of two diastereoisomers, was then dissolved in water and lyophilized. The yield was 2.1 mg (70%). TLC $R_f$ 0.14 (9:1 $CH_2Cl_2$—$CH_3OH$), 0.32 and 0.38 (85:15 $CH_2Cl_2$—$CH_3OH$); UV (95% $C_2H_5OH$) $\lambda_{max}$ 266.0 nm, $\lambda_{min}$ 235.0 nm, HPLC (gradient from 5% to 50% $CH_3CN$ in 0.05M triethylammonium acetate (TEAA) (pH= 7.0) during 40 minutes, 1.0 mL/minute) 12-fast $R_t$=20.5 minutes and 21.5 minutes, 12-slow $R_t$=33.9 min and 35.5 min. MS(FAB$^-$) 12-fast 676.7[M-B], MS(FAB$^+$)12-slow 725.6 [M+K].

D. Synthesis of oligonucleotide bearing 3',5'-[O-(o-carboran-1-yl)alkyl]phosphates, [S-(o-carboran-1-yl)alkyl]phosphorothioates, or [Se-(o-carboran-1-yl)alkyl]phosphoroselenoates internucleotide linkage.

Oligonucleotides bearing a 3',5'-[O-(carboran-1-yl)alkyl]phosphate, [S-(carboran-1-yl)alkyl]phosphorothioate, or [Se-(carboran-1-yl)alkyl]phosphoroselenoate internucleotide linkage can be conveniently synthesized using a suitable monomer such as 5'-O-monomethoxytritylnucleoside 3'-[O-(carboran-1-yl)alkyl]phosphate, [S-(carboran-1-yl)alkyl]phosphorothioate or [Se-(carboran-1-yl)alkyl]phosphoroselenoate as described previously for the oligonucleotides containing 3',5'-[(o-carboran-1-yl)alkyl]phosphonate internucleotide linkage. As known to those skilled in the art, many other groups can be used to protect the 5'-position, for example, dimethoxytrityl. The term (carboran-1-yl)alkyl refers to (o-carboran-1-yl)(lower alkyl), and in particular, (o-carboran-1-yl)(lower linear alkyl).

The monomers are prepared by the reaction of a suitably protected nucleoside with a series of new borophosphorylating agents type of O-methyl-[O-(carboran-1-yl)alkyl] phosphate (31), O-methyl-[S-(o-carboran-1-yl)alkyl]phosphorothioate (36), and O-methyl-[Se-(o-carboran-1-yl)alkyl]phosphoroselenoate (41) followed by the demethylation of the fully protected intermediates 30, 35, and 40 respectively, as described for synthesis of [O-methyl-(o-carboran-1-yl)alkyl]phosphonate previously.

The borophosphorylation reaction (synthesis of the specific monomer) proceeds under the conditions described for 5'-O-monomethoxytritylnucleoside 3'-O-methyl-[O-(o-carboran-1-yl)alkyl]phosphonate however the reaction conditions (activating agent, nucleophilic catalyst, solvent, temperature and reaction time) are adjusted in light of the substrates used.

Borophosphorylating agents type of O-methyl-[O-(o-carboran-1-yl)alkyl]phosphate (31), O-methyl-[S-(o-carboran-1-yl)alkyl]phosphorothioate (36), and O-methyl-[Se-(o-carboran-1-yl)alkyl]phosphoroselenoate (41) are prepared as follows:

O-Methyl-[O-(o-carboran-1-yl)alkyl]phosphate (31). O,O-Dimethylphosphate (25) is reacted with a suitable alcohol of the formula (n–1)-alkyn-1-ol (26) (where n=number of carbon atoms in linear hydrocarbon chain, also branched alkynes can be used) in the presence of a suitable activating agent yielding O,O-dimethyl-(O-alkynyl)phosphate (28). Another approach to intermediate 28 is based on the reaction of O,O-dimethylchlorophosphate (27) with alcohol (26) in pyridine or other proper solvent. Both reactions are performed according to well known methods of phosphorylation [Methoden der Organische Chemie, Organische Phosphor-Verbindungen (Houben-Weyl), Band XII/1 and XII/2, George Thieme Verlag, Stuttgart, 1964; also as above Band E1 and E2, 1982). The reaction of 28 with decaborane (29) and selective demethylation (removing one of methyl groups) of intermediate O,O-dimethyl-[O-(carboran-1-yl)alkyl] phosphate (30), leading to (31) can be performed as described for the synthesis of O-methyl-[(o-carboran-1-yl)alkyl]phosphonate. Another approach to (30) is based on reaction of O,O-dimethylphosphate (25) or O,O-dimethylchlorophosphate (27) with (o-carboran-1-yl)alkylol (32) as described above. (o-Carboran-1-yl)alkylol (32) can be prepared in the reaction of hydroxyl protected alkynol with dodecaborane followed by deprotection of hydroxyl function.

O-Methyl-[S-(o-carboran-1-yl)alkyl]phosphorothioate (36).

Several approaches can be used to prepare the title compound. The simplest is the alkylation reaction between O,O-dimethylphosphorothioate (33) and suitable (n-1)-alkyn-1-bromide (34) (n=number of atoms in hydrocarbon chain; linear as well as branched alkynes could be used, as well as chloride or iodide derivative), followed by the reaction with dodecaborane and selective removing of one of methyl groups [Methoden der Organische Chemie, Organische Phosphor-Verbindungen (Houben-Weyl), Band XII/1 and XII/2, George Thieme Verlag, Stuttgart, 1964; also as above Band E1 and E2, 1982).

O-methyl-[Se-(o-carboran-1-yl)alkyl]phosphoroselenoate (41).

The title compound can be prepared as described for O-methyl-[S-(o-carboran-1-yl)alkyl]phosphorothioate (36) except that O,O-dimethylphosphoroselenoate (38) is used. Another method is based on the reaction of O,O,Se-trimethylphosphoroselenoate (39) with suitable (n−1)alkyn-1-bromide (34) followed by the reaction with dodecaborane (29) or directly with [(o-carboran-1-yl)alkyl]bromide (37), followed by selective removal one of the methyl group. The second method could be used also for 36 synthesis.

E. Preparation of Oligonucleotides that contain a 3',5'-O, O-[(carboran-1-yl-methyl)phosphonate] linkage A dinucleotide containing a 3',5'-O,O-[(carboran-1-yl-methyl)phosphonate] linkage, after selective deprotection and phosphitylation of its 3'-end with 2-cyanoethyl-N,N-diisopropylchlorophosphoramidite, can be used as a building block for the synthesis of longer oligonucleotides bearing one or more alternating (carboran-1-yl)methylphosphonate linkages by automatic synthesis on solid support. See, for example, Applied Biosystems User Bulletin No. 43 1987, Applied Biosystems, Foster City, Calif. Oligonucleotides that include one or more 3',5'-O,O-[(carboran-1-yl-methyl)phosphonate] linkages can also be prepared using solution techniques as known to those skilled in the art.

Natural oligonucleotides are synthesized enzymatically on a small scale routinely. Modified oligonucleotides can be also prepared using enzymes (see Lesnikowski, Z. J., *Bioorganic Chem.*, 21:127–155 (1993)). Enzymatic synthesis of (carboranyl-1-methyl)phosphonate oligonucleotides can be carried out as a modification of the enzymatic synthesis of methylphosphonate oligonucleotide analogues (see Lesnikowski above).

F. Preparation of Oligonucleotides that contain carboranyl-containing base units As described in the Background of the Invention, nucleosides with a carboranyl moiety in the base unit have been previously reported. While useful oligonucleotides can be prepared that contain a carboranyl-containing base in any of the nucleosides, it is preferred that the carboranyl-containing base be located at the 3' or 5'-terminus or in the nucleoside adjacent to the 3' or 5'-terminal nucleoside, or in some combination thereof.

Methods for the automated production of oligonucleotides are described above. Given the disclosure herein, one of ordinary skill in the art will know how to prepare a wide variety of oligonucleotides with carboranyl-containing base units for a diverse range of applications, all of which are intended to fall within the scope of this invention. Oligonucleotides that contain one or more carboranyl-containing bases can also be prepared using solution techniques as known to those skilled in the art.

III. Method of Treatment of Urogenital Cancer with Boron Neutron Capture Therapy BNCT techniques for certain cancers other than urogenital cancers have been described in detail, for example, in Hatanaka, et al., *Z. Neurol.*, 204:309–332 (1973); Tolpin, et al., *Oncology*, 32:223–246 (1975); U.S. Pat. Nos. 5,130,302; 5,066,479, 5,021,572, 4,959,356, and 4,855,493; and Barth, et al., *Cancer Res.*, 50:1061–1070 (1990). These methods are easily adapted for use in the treatment of urogenital cancer. As an example, a patient in need thereof is treated with an effective amount of one or more $^{10}B$-containing compounds and then exposed to neutrons, preferably epithermal neutrons which should not exceed $5\times10^{12}$ n/cm$^2$ (total dose). A preferred dose of boron-containing compound, for example, a carboranyl-containing nucleoside or oligonucleotide, or combination thereof, is 0.01 to 500 mg/kg of body weight in single dose and preferably 0.1 to 100 mg/kg of body weight in a single dose administered intravenously. It may be advantageous to pulse the dosage in order to accumulate the compound in certain tumor cells. The compound can be administered at any suitable time, and is typically administered thirty minutes to one hour prior to neutron irradiation.

IV. In Vivo Analysis of $^{10}B$-Containing Compounds in Urogenital Tissue

The development of the immunodeficient athymic nude mouse has permitted the establishment of human tumors in serial transplantation which provides a representative model of the human disease state. This system, which uses the subcutaneous or subrenal capsule assay is particularly useful in assessing new therapeutic strategies in the treatment of human malignancies and ensures the availability of a constant source of non-attenuated fresh human tumor cells. Analysis of treatment efficacy can be assessed in the short term and these results can be monitored to determine the effect on host animal survival.

Nude mice studies have been successfully carried out using human prostate and bladder cancer cell lines. Keane, T. E., Rosner, G., Donaldson, J., Norwood, D., Poulton, S. H., and Walther, P. J., "Dipyridamole-cisplatin potentiation in xenograft models of human testicular and bladder cancer," *J. Urol.*, 144:1004–1009 (1990); Keane, T. E., Rosner, G., Gingrich, J., Poulton, S., and Walther, P., "The therapeutic impact of dipyridamole: chemopotentiation of the cytotoxic combination 5-fluorouracil/cisplatin in an animal model of human bladder cancer," *J. Urol.*, 146:1418–1424 (1991); Keane, T. E., Gingrich J. R., Rosner, G., Webb, K. S., Poulton, S. H., and Walther, P., "Combination versus single agent therapy in effecting complete therapeutic response in human bladder cancer: analysis of cisplatin and/or 5-fluorouracil in an in vivo survival model," *Cancer Res.*, 54:475–481 (1994); and Keane, et al., *Proceedings of the American Association for Cancer Research*, 31:376 (abst 2230) 1990.

Any of these systems can be used to evaluate the extent of accumulation of a selected boron-containing compound in a selected urogenital cancer cell line, or the effect of irradiation of the accumulated compound on that cell line. A detailed example of the evaluation of the accumulation of CDU in a xenographed human prostate tumor obtained from nude mice treated intraperitoneally with 5 mg/kg of tritiated CDU (15 µCi/mouse) is provided in Example 5.

EXAMPLE 5

In Vivo Analysis of $^{10}$B-Containing Compounds in Urogenital Tissue

To analyze the concentration of $^{10}$B-containing compounds in urogenital tissue, the tumor is removed from the animal and then lyophilized. The $^{10}$B-containing compounds are extracted with a methanol/water solution, and then counted using known methods.

Table 1 provides a summary of the accumulation of CDU in a xenographed human prostate tumor on nude mice treated intraperitoneally with 5 mg/kg of tritiated CDU (15 µCu/mouse). It was found that CDU significantly accumulates in the prostate cancer cells, and preferentially so, over brain tissue and serum. The compound partitions in a ratio of approximately 2:1 in the prostate versus blood serum.

TABLE 1

Analysis of Xenographed human Prostate Tumor Obtained from Nude mice treated intraperitoneally with 5 mg/kg of Tritiated CDU (15 µCi/mouse)

| Organ/ Fluid | Time after CDU administration (hr) | Mean DPM/mg of dry weight | pmole/mg of dry weight |
|---|---|---|---|
| Tumor | 1 | 489.1 | 3.60 |
| Brain | 1 | 42.8 | 0.32 |
| Serum | 1 | 181.0 | 1.33 |
| Tumor | 2 | 256.7 | 1.89 |
| Brain | 2 | 23.4 | 0.17 |
| Serum | 2 | 111.0 | 0.82 |

V. Pharmacokinetics of 5-Carboranyl-2'-Deoxyuridine in Rats.

The pharmacokinetics of 5-carboranyl-2'-deoxyuridine in rats was studied in detail, as described in Example 6.

EXAMPLE 6

Pharmacokinetics of CDU in Rats

Materials and methods

5-Carboranyl-2'-deoxyuridine (CDU) was synthesized by the method of Yamamoto, et al. The chemical purity, confirmed by $^1$H NMR spectral and high-pressure liquid chromatography (HPLC) analysis, was greater than 98%. For intravenous administration, CDU was dissolved in dimethylsulfoxide (DMSO). Internal standard, progesterone, and β-glucuronidase were purchased from Sigma Chemical Company (St. Louis, Mo.). Methanol, HPLC grade, and all other chemicals, analytical grade, were obtained from J. T. Baker (Phillipsburg, N.J.). Partition coefficients were determined one hour after administration.

The partition coefficient (P) of CDU was determined in octanol:phosphate buffer (pH 7.4). The octanol and aqueous phases were equilibrated by shaking together for 1 hour at 20° C. Two milliliters (2 ml) of octanol containing 0.5 mg/ml of CDU were shaken with 4 ml of buffer on a horizontal shaker for 12 hour at 25° C. Tubes were centrifuged to separate the phases and both phases were analyzed by HPLC as described below. The partition coefficient was calculated by dividing the CDU concentration in octanol by the CDU concentration in buffer. Results are reported as log P values.

Five adult male Sprague-Dawley (Harlan Laboratories, Indianapolis, Ind.) rats weighing 303±8 g (mean±SD) were used for the pharmacokinetic study. Rats were housed in a 12 hour light/12 hour dark, constant temperature (22° C.) environment with free access to standard laboratory chow and water. Animals were acclimatized to this environment for one week before the experiment. External jugular vein cannulas were implanted under ketamine:acepromazine:xylazine (50:3.3:3.3 mg/kg) anesthesia the day before the experiment. Rats were fasted overnight, however, water was available ad libitum.

On the morning of the experiment, rats were placed in individual metabolism cages. CDU 925 mg/kg) was administered intravenously in 0.1 ml of DMSO to the rats over a one minute period. Blood samples (0.35 ml) were collected prior to and at 0.25, 0.5, 0.75, 1, 1.15, 2, 3, 4, 5, 6, 7 and 8 hour after CDU administration from the cannula into heparinized polypropylene microcentrifuge tubes. Blood volume was replaced with an equal volume of normal saline. Blood samples were immediately centrifuged at 2000 g for 5 minutes and plasma was separated and frozen at −20° C. until analysis. Urine was collected for 24 hour following CDU administration. Urine volume was measured and samples were frozen at −20° C. until analysis.

Protein binding was determined by equilibrium dialysis. Various amounts of CDU were added to drug free rat plasma to yield CDU concentrations ranging from 0.5 to 100 µg/ml. Plexiglass dialysis cells and dialysis membrane (Spectrapor II, Spectrum Medical Industries, Los Angeles, Calif.) were used. Plasma (0.8 ml) containing different concentrations of CDU was dialyzed against 0.8 ml of isotonic sodium phosphate buffer, pH 7.4, in a shaking water bath at 37° C. for 16 hours. The post-dialysis plasma and buffer volumes were measured and samples were frozen at −20° C. until analysis. The binding data was corrected for fluid shifts that occurred during dialysis. Experiments were performed in duplicate.

Two adult male sprague-dawley rats weighing 305 and 312 g were used to examine the brain uptake of CDU. A loading dose of 5 mg/kg CDU in 50 µg of DMSO was administered intravenously over a one minute period followed by three hour infusion of CDU at the rate of 5 mg/h/kg (50 µl/h) using an infusion lamp. At the end of infusion blood samples were collected and rats were sacrificed. The brains were dissected and frozen at −20° C. until analysis.

Concentrations of CDU in plasma, brain, and urine were determined by HPLC. For the determination of CDU in brain, the brain tissue was homogenized in a 1:2 (g:ml) ratio with isotonic sodium phosphate buffer, pH 7.4. To 200 µl of plasma or brain homogenate in a glass test tube, 50 µl of internal standard (20 µg/ml progesterone) and 5 ml of methylene chloride was added. Tubes were shaken for 15 minutes at low speed on a shaker, centrifuged for 5 minutes at 2000 rpm, and the plasma layer was aspirated off using a vacuum system. The remaining methylene chloride was transferred to a glass culture tube and evaporated to dryness under a stream of nitrogen gas at ambient temperature. The residue was reconstituted with 250 µl of methanol and injected onto HPLC system.

For the determination of unchanged CDU in urine, urine samples were diluted 1:50 with distilled deionized water and 100 µl of internal standard (50 µg/ml progesterone) was added and injected onto the HPLC. Concentrations of CDU glucuronide in urine were determined after hydrolyzing the glucuronate with β-glucuronidase as previously described. Glucuronide concentrations were calculated as the difference between CDU concentrations measured after hydrolysis and before hydrolysis with β-glucuronidase.

Chromatography was performed on a Hypersil ODC column (5 μm particle size, 4.6×150 mm; Alltech Associates Inc., Deerfield, Ill.) with an online guard column and an isocratic mobile phase of 65% methanol in 10 mM monobasic potassium phosphate, pH 6.3 at a flow rate of 1.5 ml/min. Compounds were detected at a UV wavelength of 274 nm with a detector range setting of 0.005 absorbance units, full scale.

The retention times of CDU and internal standard were 4.7 and 8.6 min, respectively. Sample CDU concentrations were calculated from the slope of calibration plots of the peak area ratio of CDU:internal standard versus standard CDU concentrations. The slopes and intercepts were generated using weighted ($1/x^2$) least-squares regression analysis. Standard curves were linear in the range of 0.1 μg/ml to 50 μg/ml. The intra- and inter-day relative standard deviations over the range of standard concentrations in all biological media were less than 10%. The extraction recoveries of CDU and progesterone were 99% and 95%, respectively.

Area/moment analysis was used to calculate pharmacokinetic parameters of CDU. The area under the plasma concentration-time curve (AUC) and first non-normalized moment (AUMC) were determined by Lagrange polynomial interpolation and integration from zero to the last measured sample time with extrapolation to time infinity using the least squares terminal slope. Half-life ($t_{1/2}$) was calculated from $0.693/\lambda_z$, where $\lambda_z$ is the terminal phase slope. Total clearance ($CL_T$) was calculated from Dose/AUC and steady-state volume of distribution (Vss) from $CL_T \times MRT$. Free clearance ($CL_f$) was calculated from $CL_T/f_u$ and free steady-state volume of distribution ($Vss_f$) from $Vss/f_u$, where $f_u$ is the unbound fraction in plasma.

The average octanol:phosphate buffer, pH 7.4, P value was determined to be 3090. This corresponds to a log P of CDU in octanol:phosphate buffer, pH 7.4 of 3.49, indicating that CDU is highly lipophilic.

Mean plasma concentrations of CDU as a function of time following intravenous administration of 25 mg/kg CDU to rats were studied. Plasma concentrations of the boron containing nucleoside analogue declined in a biexponential fashion with a terminal half-life of 1.26±0.28 hour (mean±SD). The plasma protein binding of CDU was independent of the nucleoside concentration and the average fraction bound to the plasma proteins was 0.95±0.02.

Individual, as well as mean, pharmacokinetic parameter values for CDU are presented in Table 2. The total clearance of the compound was 0.69±0.2 l/h/kg. Clearance based on unbound plasma CDU concentrations ($CL_f$) was much greater averaging 15.33±4.44 l/h/kg. No unchanged CDU was detected in urine collected for 24 hours following drug administration. In addition, there was no trace of CDU glucuronide in urine as determined indirectly by hydrolysis treatment of urine with β-glucuronidase.

The steady-state volume of distribution of CDU was 0.70±0.23 l/kg. Following intravenous infusion to steady-state, total plasma CDU concentrations were 5.92 and 5.01 μg/ml in the two rats studied while brain CDU concentrations were 2.77 μg/ml and 1.81 μg/ml. Thus, the brain:total plasma CDU concentration ratios were 0.47 and 0.36 for the two rats. Brain:unbound plasma CDU ratios were 10.26 and 7.87.

CDU was highly bound to plasma proteins (95.5%) in a linear manner over the CDU concentration range of 0.5 μg/ml to 100 μg/ml. This concentration range encompassed those observed following intravenous administration of 25 mg/kg CDU to rats. Assuming that the lipophilic compound CDU is bound predominantly by hydrophobic interactions to albumin, the equilibrium association constant for the protein binding of CDU was approximately $4 \times 10^4$ $M^{-1}$.

No unchanged CDU was recovered in urine indicating the compound is not renally excreted to any significant extent by the rat. These results indicate that CDU undergoes virtually complete renal tubular reabsorption. Typically, nucleoside analogues, such as 3'-azido-3'-deoxythymidine (AZT) and 3'-azido-2',3'-dideoxyuridine (AZddU), are not reabsorbed appreciably by the renal tubule. However, owing to the highly lipophilic nature of CDU, this nucleoside is susceptible to passive tubular reabsorption. Non-renal clearance mechanisms, therefore, account for the total clearance of CDU. While the metabolic profile for CDU was not fully assessed, no glucuronide metabolites were detected in urine samples. However, this does not rule out the possibility that CDU is glucuronidated in the rat, since this metabolite may be eliminated via biliary excretion.

The total clearance of CDU (0.69 l/h/kg) was moderate relative to hepatic blood flow (2.9 l/h/kg) of the rat. Assuming that CDU is eliminated exclusively by hepatic metabolism, the intrinsic metabolic clearance of CDU was 0.9 l/h/kg. The clearance of CDU based on unbound drug concentrations was relatively high, averaging 15.3 l/h/kg. The estimated metabolic intrinsic clearance of free drug was 20 l/h/kg. Thus, the total clearance of CDU is limited by the high degree of plasma protein binding of the nucleoside analogue resulting in a moderate total clearance value.

The steady state volume of distribution of CDU based on total drug concentrations in plasma was moderate averaging 0.7 l/kg. However, the volume of distribution based on unbound CDU concentrations was relatively high (15.5 l/kg). These results indicate that the unbound CDU distributes readily throughout the body, although the overall distribution of the compound is restricted by the high degree of plasma protein binding of CDU. The penetration of CDU into the brain was also restricted by plasma protein binding. Brain:plasma CDU concentration ratios were 20-fold greater based on unbound plasma CDU concentrations compared to those determined for total plasma concentrations of the compound. Despite the high degree of plasma protein binding of CDU, brain concentrations of the nucleoside were 36 to 47% of total plasma CDU concentrations. Thus, relatively high concentrations of the boron containing nucleoside analogue were found in the brain.

TABLE 2

Pharamacokinetic parameters for CDU following intravenous administration of 25 mg/kg CDU to rats

| Rat Number | Weight (g) | AUC (mg h l$^{-1}$) | $t_{1/2}$ (h) | MRT (h) | $CL_T$ (1 h$^{-1}$ kg$^{-1}$) | $V_{ss}$ (1 kg$^{-1}$) | $CL_f$ (1 h$^{-1}$ kg$^{-1}$) | $V_{ss,f}$ (1 kg$^{-1}$) |
|---|---|---|---|---|---|---|---|---|
| 1 | 291 | 32.39 | 1.46 | 1.17 | 0.77 | 0.90 | 17.15 | 20.02 |
| 2 | 304 | 25.14 | 1.20 | 0.51 | 0.99 | 0.51 | 22.33 | 11.29 |
| 3 | 298 | 44.68 | 0.81 | 0.81 | 0.56 | 0.45 | 12.36 | 10.09 |
| 4 | 306 | 42.49 | 1.54 | 1.64 | 0.59 | 0.97 | 13.07 | 21.56 |
| 5 | 314 | 47.28 | 1.28 | 1.24 | 0.53 | 0.65 | 11.76 | 14.53 |
| Mean | 303 | 38.39 | 1.26 | 1.07 | 0.69 | 0.70 | 15.33 | 15.50 |
| SD | 8 | 9.31 | 0.28 | 0.43 | 0.20 | 0.23 | 4.44 | 5.13 |

EXAMPLE 7

Toxicity of CDU and CFAU

A toxicity study was conducted on 6-week-old Swiss female mice treated with CDU and CFAU at 30 mg/kg/day. The compounds were prepared in sterile DMSO and injected intraperitoneally (0.1 mL). DMSO and water were used as controls, with the same injection volume as that used for the CDU and CFAU solutions. The dosing schedule used was once a day for 6 days, and the mice were weighed biweekly for 28 days. Results shown in Table 3 somewhat correlate with the cytotoxicity assays in vitro. Although CFAU and CDU produced comparable weight loss after 1 week, CFAU appeared to be more toxic than CDU as monitored by survival outcome. At 4 weeks, all the surviving animals recovered their weight loss to control untreated levels.

TABLE 3

Effect of CDU and CFAU on Survival of Normal Swiss Mice (30 mg/kg/day, QD × 6d)

| compd | % of weight gained or lost on week | | | | survival at week 4, alive/total (%) |
|---|---|---|---|---|---|
| | 1 | 2 | 3 | 4 | |
| CDU | −7.4 | 0.1 | 4.8 | 11.2 | 5/5 (100) |
| CFAU | −6.8 | −0.4 | 5.0 | 9.6 | 4/5 (80)[a] |
| DMSO | −0.9 | 3.0 | 6.3 | 10.0 | 5/5 (100) |
| H$_2$O | 6.1 | 7.8 | 10.2 | 13.1 | 5/5 (100) |

[a]Death of mouse occurred on day 7.

EXAMPLE 8

Detection of Boron in Tissue Samples

The technique developed by Gabel, et al. is used, in which cellulose nitrate film is used to detect ng amounts of natural boron in 0.5 mg. droplets (Gabel, D., Hocke, I., and Elsen, W., "Determination of sub-ppm amounts of boron-10 solutions by means of solid state track detectors," *Phys. Med. Biol.*, 28:1453–1457 (1983); Fairchild, R. G., Gabel, D., Laster, B., and Kiszenick, W. "B-10 Analysis in Tissue by Prompt-gamma and Track Etching Techniques", Proc. the First International Symposium on Neutron Capture Therapy, Oct. 12–14, 1983. *BNL Report No.* 51730, 106–13 (1984). Small (0.5 μl) droplets containing known or unknown amounts of boron are deposited on cellulose nitrate film (kodak Pathe type LR115), dried, and then irradiated with ≈6×10$^{12}$ n/cm$^2$. The resulting alpha tracks are etched with NaOH, and then counted optoelectronically. The boron content in 10$^6$ cells (≅1 mg of tissue or sample) can be obtained by lysing the cells to be analyzed, and then proceeding as described above. This procedure can be easily adapted by one of skill in the art for diagnosis using the boron containing probes.

VIII. Antisense Therapy

Oligonucleotides of the present invention which are capable of binding to polyribonucleic acid or polydeoxyribonucleic acid are useful as antisense agents in the same manner as conventional antisense agents. See generally "Antisense Molecular Biology and S-oligos, *Synthesis* 1," October 1988 (published by Synthecell Corp., Rockville, Md.); "2 Discoveries in Antisense Nucleic Acids" (C. Brakel and R. Fraley eds. 1989); Uhlmann, et al., "Antisense Oligonucleotides: A New Therapeutic Technique," *Chem. Rev.*, 90(4) (1990); and Milligan, J. F., Matteucci, M. D., Martin, J. C., *J. Med. Chem.*, 36:1923–1937 (1993). Antisense agents of the present invention may be used by constructing an antisense agent which is capable of selectively binding to a predetermined polydeoxyribonucleic acid sequence or polyribonucleic acid sequence to a cell containing such sequence (such as by adding the antisense agent to a culture medium containing the cell) so that the antisense agent is taken into the cell, binds to the predetermined sequence, and blocks transcription, translation, or replication thereof. The requirements for selective binding of the antisense agent are known (such as a length of 17 bases for selective binding within the human genome).

IX. Pharmaceutical Compositions and Delivery of Boron-Containing Compounds $^{10}$B-Containing compounds can be administered to humans in an effective amount for treatment of urogenital cancer using BNCT, optionally in combination with AOT. The boron-containing agent can be optionally be administered as a pharmaceutically acceptable derivative or salt, or if desired, in combination with a pharmaceutically acceptable carrier or diluent. The active materials can be administered by any appropriate route, for example, orally, parenterally, intravenously, intradermally, subcutaneously, or topically, in liquid or solid form.

The active compound is included in the pharmaceutically acceptable carrier or diluent in an amount sufficient to achieve the desired therapeutic result without causing serious toxic effects in the patient treated. The compound should have a therapeutic index of at least 2, and preferably at least 5 or 10, are acceptable. The therapeutic index is defined as the IC$_{50}$/EC$_{50}$, wherein EC$_{50}$ is the concentration of compound that inhibits the growth by 50% of the diseased cells and IC$_{50}$ is the concentration of compound that is toxic to 50% of the otherwise healthy target cells. Cellular toxicity can be measured by direct cell counts, trypan blue exclusion, or various metabolic activity studies such as $^3$H-thymidine incorporation, as known to those skilled in the art.

A preferred dose of the active compound for all of the above-mentioned conditions will be in the range of 0.01 and between approximately 500 and 1000 mg/kg of body weight and preferably 0.1 to between approximately 20 and 100 mg/kg of body weight in a single dose per day. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The compound is conveniently administered in any suitable dosage form, including but not limited to one containing 5 to 3000 mg, preferably 70 to 1400 mg of active ingredient per unit dosage form. A oral dosage of 50–1000 mg is usually convenient.

Ideally the active ingredient should be administered to achieve peak plasma concentrations of the active compound of from about 0.01 to 400 μM, preferably about 0.1 to 100 μM. This may be achieved, for example, by the intravenous injection of a 0.1 to 5% solution of the active ingredient, optionally in saline, or administered as a bolus of the active ingredient.

In a preferred embodiment for BNCT, the active compound is administered in an intravenous solution with a dose ranging from 1 mg/kg to 100 mg/kg. In a preferred embodiment for antisense therapy, the active compound is administered in a pharmaceutical composition for oral delivery that protects the compound from the acid environment of the stomach, for example, an enteric coating.

The concentration of active compound in the drug composition will depend on absorption, inactivation, and excretion rates of the drug as well as other factors known to those of skill in the art. It is to be noted that, when using the compound to treat a disease, dosage values will vary depending on the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The active compound or a pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable derivative or salt thereof can also be mixed with other active materials that do not impair the desired action, or with materials that supplement the desired action, such as antibiotics, antifungals, antiinflammatories, or other antivirals, including other nucleoside anti-HIV compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Scios-Nova Pharmaceuticals, Inc.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

This invention has been described with reference to its preferred embodiments. variations and modifications of the invention will be obvious to those skilled in the art from the foregoing detailed description of the invention. It is intended that all of these variations and modifications be included within the scope of the appended claims.

We claim:

1. A method for treating a urogenital tumor in a human, comprising administering to the tumor being human an effective amount of a $^{10}$B-containing compound, and irradiating the tumor with sufficient low energy neutrons to achieve cytotoxicity.

2. The method of claim 1 wherein the urogenital tumor is in the prostate.

3. The method of claim 1 wherein the urogenital tumor is in the bladder.

4. The method of claim 1 wherein the urogenital tumor is in the kidney.

5. The method of claim 1, wherein the $^{10}$B-containing compound is selected from the group consisting of 5-carboranyl-2'-deoxyuridine and 5-o-carboranyl-1-(2-deoxy-2-fluoro-β-D-arabinofuranosyl)uracil.

6. The method of claim 1, wherein the $^{10}$B-containing compound is selected from the group consisting of:

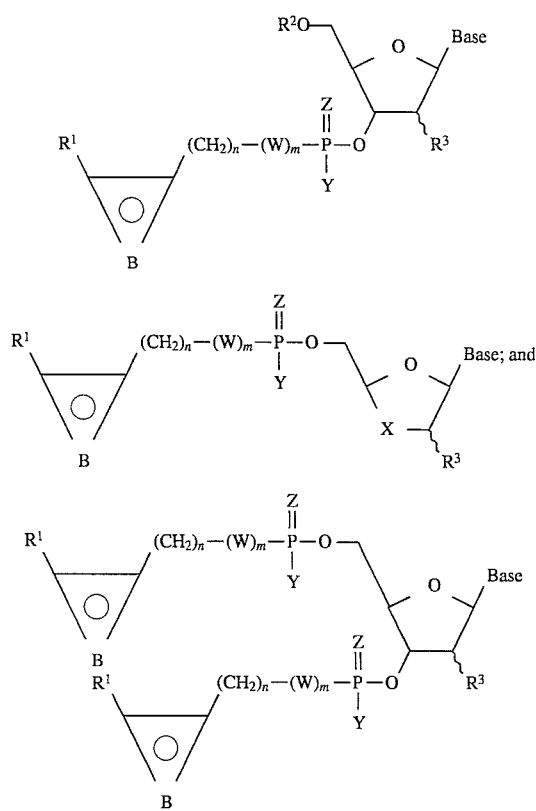

wherein $R^1$ is alkyl, haloalkyl, alkenyl, alkoxyalloyl, aryl, heteroaryl, trifluoromethyl, alkylaryl, arylalkyl, or halogen;

$R^2$ is hydrogen, alkyl, acyl; sulfonate ester; a mono, di or triphosphate ester; trityl or monomethoxytrityl; benzyl optionally substituted with one or more aryl substituents; silyl, or diphenylmethylsilyl; lipid; peptide; or cholesterol;

$R^3$ is hydroxyl, hydrogen, halogen, —CN, —N$_3$, lower alkyl, amino, alkylamino, dialkylamino, alkoxy; and wherein the $R^3$ group can be in the ribosyl or the arabinosyl conformation;

B represents the boron moiety of a carboranyl group;

W is O, S, or Se;

X is O, S, S(O), S(O)$_2$, CH$_2$, CHOH, CHN$_3$ or NH;

Y is OH, SH, SeH, or halogen;

Z=O or S;

n is 1–5;

m is 0 or 1; and base refers to a purine or pyrimidine.

7. The method of claim 1, wherein the $^{10}$B-containing compound is selected from the group consisting of

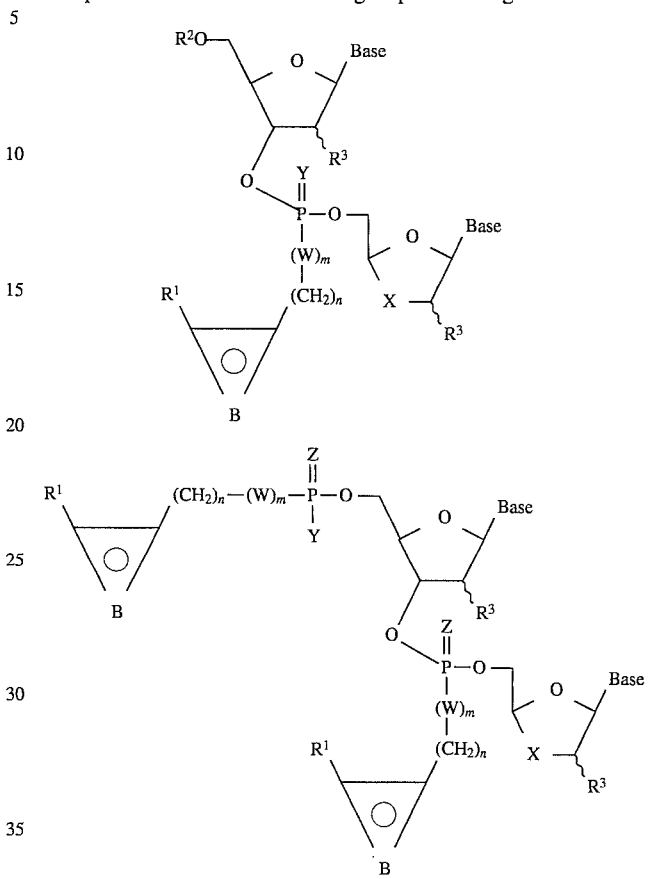

wherein $R^1$ is alkyl, haloalkyl, alkenyl, alkoxyalloyl, aryl, heteroaryl, trifluoromethyl, alkylaryl, arylalkyl, or halogen;

$R^2$ is hydrogen, alkyl, acyl; sulfonate ester; a mono, di or triphosphate ester; trityl or monomethoxytrityl; benzyl optionally substituted with one or more aryl substituents; silyl, or diphenylmethylsilyl; lipid; peptide; or cholesterol;

$R^3$ is hydroxyl, hydrogen, halogen, —CN, —N$_3$, lower alkyl, amino, alkylamino, dialkylamino, alkoxy; and wherein the $R^3$ group can be in the ribosyl or the arabinosyl conformation;

B represents the boron moiety of a carboranyl group;

W is O, S, or Se;

X is O, S, S(O), S(O)$_2$, CH$_2$, CHOH, CHN$_3$ or NH;

Y is OH, SH, SeH, or halogen;

Z=O or S;

n is 1–5;

m is 0 or 1;

and wherein "base" refers to a purine or pyrimidine.

8. The method of claim 7 wherein the base is selected from the group consisting of thymine, uracil, 5-halouracil, cytosine, 5-halocytosine, 6-azapyrimidine, adenine, guanine, 2,6-diaminopurine, 2-amino-6-chloropurine, 2-aminopurine, 5-lower alkyl uracil, 5-lower alkylcytosine, 2-thiouracil, 2,4-thiouracil, 4-thiouracil, 6-chloropurine, 5-carboranyluracil, and 5-carboranylcytosine.

9. The method of claim 1 wherein the $^{10}$B-containing compound is an oligonucleotide.

10. The method of claim 1 wherein the $^{10}$B-containing compound is a nucleoside selected from the group consisting of:

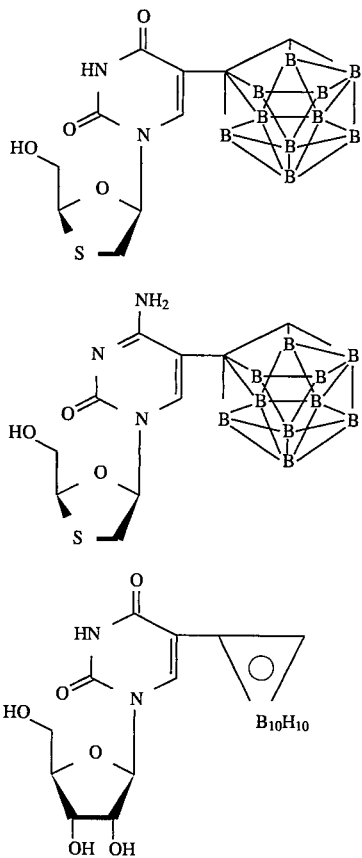

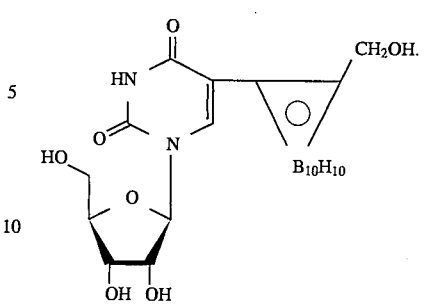

11. The method of claim 6, wherein B is selected from the group consisting of anionic o-nido-7,8-$C_2B_9H_{(11\ or\ 12)}$ and neutral o-closo-1,2-$C_2B_{10}H_{12}$.

12. The method of claim 7, wherein B is selected from the group consisting of anionic o-nido-7,8-$C_2B_9H_{(11\ or\ 12)}$ and neutral o-closo-1,2-$C_2B_{10}H_{12}$.

13. A method for treating a urogenital tumor in a host animal, comprising administering to the tumor bearing host animal an effective amount of a $^{10}$B-containing compound, and irradiating the tumor with sufficient low energy neutrons to achieve cytotoxicity.

14. The method of claim 6 wherein $R^2$ is acetyl.

15. The method of claim 6 wherein $R^2$ is trialkylsilyl.

16. The method of claim 6 wherein B is anionic o-nido-7,8-$C_2B_9H_{(11\ or\ 12)}$.

17. The method of claim 6 wherein B is neutral o-closo-1,2-$C_2B_{10}H_{12}$.

18. The method of claim 7 wherein $R^2$ is acetyl.

19. The method of claim 7 wherein $R^2$ is trialkylsilyl.

20. The method of claim 7 wherein B is anionic o-nido-7,8-$C_2B_9H_{(11\ or\ 12)}$.

21. The method of claim 7 wherein B is neutral o-closo-1,2-$C_2B_{10}H_{12}$.

* * * * *